US012788389B2

(12) United States Patent
McAlister et al.

(10) Patent No.: US 12,788,389 B2
(45) Date of Patent: Nov. 10, 2026

(54) BIOLOGICAL FLUID DRAINAGE DEVICES, SYSTEMS, AND METHODS

(71) Applicant: W.L. Gore & Associates, Inc., Newark, DE (US)

(72) Inventors: Jesse R. McAlister, Newark, DE (US); Kevin M. Savory, West Grove, PA (US); Jeffrey C. Towler, Wilmington, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 778 days.

(21) Appl. No.: 18/096,151

(22) Filed: Jan. 12, 2023

(65) Prior Publication Data

US 2023/0218286 A1 Jul. 13, 2023

Related U.S. Application Data

(60) Provisional application No. 63/298,854, filed on Jan. 12, 2022.

(51) Int. Cl.
*A61B 17/04* (2006.01)
*A61B 17/00* (2006.01)

(52) U.S. Cl.
CPC ........ *A61B 17/04* (2013.01); *A61B 17/00234* (2013.01)

(58) Field of Classification Search
CPC ... A61B 17/04; A61B 17/00234; A61B 3/165; A61F 9/00781; A61F 9/0017;
(Continued)

(56) References Cited

U.S. PATENT DOCUMENTS 3,618,604 A 11/1971 Ness
3,683,928 A 8/1972 Kuntz
(Continued)

FOREIGN PATENT DOCUMENTS

AU 06600/12 B2 6/1995
AU 2014280907 A1 1/2015
(Continued)

OTHER PUBLICATIONS

Doble, M., Makadia, N., Pavithran, S., & Kumar, R. S. (2008). Analysis of explanted ePTFE cardiovascular grafts (modified BT shunt). Biomedical Materials, 3(3), 034118. (Year: 2008).
(Continued)

*Primary Examiner* — Aaron F Roane
(74) *Attorney, Agent, or Firm* — Crowell & Moring LLP

(57) ABSTRACT

Drainage device for draining a biological fluid from an eye to a tissue external to the eye, as well as methods of forming the drainage device and treating glaucoma using the drainage device, are disclosed. The drainage device is implantable at least in part within a tissue of the eye and includes a collapsible body portion defining a reservoir, and a conduit having a first end fluidly coupled with the reservoir and a second end insertable into the eye to facilitate a drainage of the biological fluid into the conduit. When collapsed, the body portion includes a deformation from a first planar state to a second nonplanar state, where the second nonplanar state may be a folded, deformed, bent, or crumpled state.

36 Claims, 18 Drawing Sheets

(58) Field of Classification Search
CPC .... A61F 2009/00891; A61F 2250/0051; A61F 2250/0024; A61K 9/0051; A61M 2210/0612; A61M 27/002
USPC .............................................................. 606/1
See application file for complete search history.

(56) References Cited

U.S. PATENT DOCUMENTS 3,828,777 A 8/1974 Ness
3,960,150 A 6/1976 Hussain et al.
3,962,414 A 6/1976 Michaels
4,014,335 A 3/1977 Arnold
4,182,342 A 1/1980 Smith
4,186,184 A 1/1980 Zaffaroni
4,554,918 A 11/1985 White
4,579,221 A 4/1986 Corella
4,729,761 A 3/1988 White
4,759,759 A 7/1988 Walker et al.
4,946,436 A 8/1990 Smith
5,026,395 A 6/1991 Nakajima et al.
5,037,434 A 8/1991 Lane
5,147,647 A 9/1992 Darougar
5,163,955 A 11/1992 Love et al.
5,282,851 A 2/1994 Jacob-LaBarre
5,378,475 A 1/1995 Smith et al.
5,423,777 A 6/1995 Tajiri et al.
5,476,445 A 12/1995 Baerveldt et al.
5,676,679 A 10/1997 Simon et al.
5,681,275 A 10/1997 Ahmed
5,702,414 A 12/1997 Richter et al.
5,708,044 A 1/1998 Branca
5,713,953 A 2/1998 Vallana et al.
5,752,928 A * 5/1998 de Roulhac ......... A61F 9/00781 604/9
5,773,019 A 6/1998 Ashton et al.
5,861,028 A 1/1999 Angell
5,882,327 A 3/1999 Jacob
5,928,281 A 7/1999 Huynh et al.
5,935,163 A 8/1999 Gabbay
6,050,970 A 4/2000 Baerveldt
6,074,419 A 6/2000 Healy et al.
6,086,612 A 7/2000 Jansen
6,142,969 A 11/2000 Nigam
6,171,335 B1 1/2001 Wheatley et al.
6,174,331 B1 1/2001 Moe et al.
6,186,974 B1 2/2001 Allan et al.
6,197,143 B1 3/2001 Bodnar
6,254,636 B1 7/2001 Peredo
6,261,256 B1 7/2001 Ahmed
6,283,995 B1 9/2001 Moe et al.
6,287,338 B1 9/2001 Sarnowski et al.
6,364,905 B1 4/2002 Simpson et al.
6,432,542 B1 8/2002 Tsai
6,450,984 B1 9/2002 Lynch et al.
6,471,689 B1 10/2002 Joseph et al.
6,541,589 B1 4/2003 Baillie
6,562,069 B2 5/2003 Cai et al.
6,562,446 B1 5/2003 Totsuka
6,613,086 B1 9/2003 Moe et al.
6,613,087 B1 9/2003 Healy et al.
6,696,526 B1 2/2004 Kaulbach et al.
6,699,210 B2 3/2004 Williams et al.
6,699,211 B2 3/2004 Savage
6,713,081 B2 3/2004 Robinson et al.
6,881,197 B1 * 4/2005 Nigam ................ A61M 27/006 604/9
6,994,666 B2 2/2006 Shannon et al.
7,018,404 B2 3/2006 Holmberg et al.
7,261,732 B2 8/2007 Justino
7,306,729 B2 12/2007 Bacino et al.
7,320,705 B2 1/2008 Quintessenza
7,331,993 B2 2/2008 White
7,361,189 B2 4/2008 Case et al.
7,462,675 B2 12/2008 Chang et al.
7,531,611 B2 5/2009 Sabol et al.
7,604,663 B1 10/2009 Reimink et al.
7,833,565 B2 11/2010 O'Connor et al.
7,862,610 B2 1/2011 Quintessenza
7,883,717 B2 2/2011 Varner et al.
8,216,631 B2 7/2012 O'Connor et al.
8,219,229 B2 7/2012 Cao et al.
8,246,676 B2 8/2012 Acosta et al.
8,267,994 B2 9/2012 Jin
8,273,101 B2 9/2012 Garcia et al.
8,303,647 B2 11/2012 Case
8,399,006 B2 3/2013 De Juan, Jr. et al.
8,545,430 B2 10/2013 Silvestrini
8,556,960 B2 10/2013 Agnew et al.
8,623,395 B2 1/2014 De et al.
8,632,489 B1 1/2014 Ahmed
8,637,144 B2 1/2014 Ford
8,690,939 B2 4/2014 Miller et al.
8,834,406 B2 9/2014 Snyder et al.
8,834,911 B2 9/2014 Glezer et al.
8,888,734 B2 11/2014 Nissan et al.
8,961,593 B2 2/2015 Bonhoeffer et al.
8,961,599 B2 2/2015 Bruchman et al.
8,961,600 B2 2/2015 Nissan et al.
9,139,669 B2 9/2015 Xu et al.
9,155,610 B2 10/2015 Soletti et al.
9,155,618 B2 10/2015 Kalmann et al.
9,216,108 B2 12/2015 Jain et al.
9,259,313 B2 2/2016 Wheatley
9,301,835 B2 4/2016 Campbell et al.
9,301,837 B2 4/2016 Beith
9,326,891 B2 5/2016 Horvath et al.
9,364,322 B2 6/2016 Conklin et al.
9,370,444 B2 6/2016 Cunningham, Jr.
9,375,347 B2 6/2016 Stergiopulos
9,539,089 B2 1/2017 Beith
9,572,713 B2 2/2017 Lind et al.
9,636,219 B2 5/2017 Keidar et al.
9,636,254 B2 5/2017 Yu et al.
9,655,720 B2 5/2017 Bluestein et al.
9,675,453 B2 6/2017 Guttenberg et al.
9,833,314 B2 12/2017 Corbett
9,849,629 B2 12/2017 Zagl et al.
9,987,120 B2 6/2018 Soletti et al.
9,999,500 B2 6/2018 Greenslet et al.
10,052,200 B2 8/2018 Chung et al.
10,195,023 B2 2/2019 Wrobel
10,299,915 B2 5/2019 Edelman et al.
10,307,292 B2 6/2019 Litvin
10,398,593 B2 9/2019 Erickson et al.
10,398,707 B2 9/2019 Hughes
10,413,402 B2 9/2019 Squara
10,413,403 B2 9/2019 Boden et al.
10,426,609 B2 10/2019 Edelman et al.
10,433,955 B2 10/2019 Edelman et al.
10,512,537 B2 12/2019 Corbett et al.
10,588,746 B2 3/2020 Bernstein et al.
10,603,164 B2 3/2020 Girard et al.
10,849,731 B2 12/2020 Cully et al.
10,959,941 B2 3/2021 Haffner
11,351,058 B2 6/2022 Roeber et al.
11,406,533 B2 8/2022 Roeber et al.
11,523,940 B2 12/2022 Roeber et al.
2002/0106395 A1 8/2002 Brubaker
2002/0110635 A1 8/2002 Brubaker et al.
2002/0156413 A1 10/2002 Williams et al.
2002/0165478 A1 11/2002 Gharib et al.
2002/0198594 A1 12/2002 Schreck
2003/0014036 A1 1/2003 Varner et al.
2003/0027332 A1 2/2003 Lafrance et al.
2003/0088260 A1 5/2003 Smedley et al.
2003/0094731 A1 5/2003 Simpson
2003/0109923 A1 6/2003 Chinn et al.
2003/0229303 A1 12/2003 Haffner et al.
2004/0024345 A1 2/2004 Gharib et al.
2004/0215333 A1 10/2004 Duran et al.
2005/0085892 A1 4/2005 Goto et al.
2005/0106211 A1 5/2005 Nelson et al.
2005/0137538 A1 6/2005 Kunzler et al.
2005/0171507 A1 8/2005 Christian et al.

(56) References Cited

U.S. PATENT DOCUMENTS

| | | | |
|---|---|---|---|
| 2005/0182350 | A1 | 8/2005 | Nigam |
| 2005/0228487 | A1 | 10/2005 | Kujawski |
| 2005/0234546 | A1 | 10/2005 | Nugent et al. |
| 2005/0244465 | A1 | 11/2005 | Nivaggioli et al. |
| 2005/0250788 | A1 | 11/2005 | Tu et al. |
| 2005/0261759 | A1 | 11/2005 | Lambrecht et al. |
| 2005/0266047 | A1 | 12/2005 | Tu et al. |
| 2005/0267398 | A1 | 12/2005 | Protopsaltis et al. |
| 2005/0273033 | A1 | 12/2005 | Grahn et al. |
| 2006/0036207 | A1 | 2/2006 | Koonmen et al. |
| 2006/0109923 | A1 | 5/2006 | Cai et al. |
| 2006/0110429 | A1 | 5/2006 | Reiff et al. |
| 2006/0189917 | A1 | 8/2006 | Mayr et al. |
| 2006/0195187 | A1 | 8/2006 | Stegmann et al. |
| 2006/0258994 | A1 | 11/2006 | Avery |
| 2007/0077270 | A1 | 4/2007 | Wen |
| 2007/0078371 | A1 | 4/2007 | Brown et al. |
| 2007/0083184 | A1 | 4/2007 | Simpson |
| 2007/0088432 | A1 | 4/2007 | Solovay et al. |
| 2007/0118147 | A1 | 5/2007 | Smedley et al. |
| 2007/0207186 | A1 | 9/2007 | Scanlon et al. |
| 2007/0219632 | A1 | 9/2007 | Castillejos |
| 2007/0293872 | A1 | 12/2007 | Peyman |
| 2008/0071361 | A1 | 3/2008 | Tuval et al. |
| 2008/0082161 | A1 | 4/2008 | Woo |
| 2008/0091261 | A1 | 4/2008 | Long et al. |
| 2008/0133005 | A1 | 6/2008 | Andrieu et al. |
| 2008/0147021 | A1 | 6/2008 | Jani |
| 2008/0200977 | A1 | 8/2008 | Paul et al. |
| 2008/0264993 | A1 | 10/2008 | Schulte et al. |
| 2008/0268314 | A1 | 10/2008 | Han et al. |
| 2008/0312737 | A1 | 12/2008 | Jin |
| 2009/0043321 | A1 | 2/2009 | Conston et al. |
| 2009/0155326 | A1 | 6/2009 | Mack et al. |
| 2009/0157175 | A1 | 6/2009 | Benichou |
| 2009/0226731 | A1 | 9/2009 | Wittmann et al. |
| 2009/0227933 | A1 | 9/2009 | Karageozian |
| 2009/0240215 | A1 | 9/2009 | Humayun et al. |
| 2009/0240320 | A1 | 9/2009 | Tuval et al. |
| 2009/0299469 | A1 | 12/2009 | Kollar |
| 2010/0015200 | A1 | 1/2010 | Mcclain et al. |
| 2010/0082094 | A1 | 4/2010 | Quadri et al. |
| 2010/0114006 | A1 | 5/2010 | Baerveldt |
| 2010/0114307 | A1 | 5/2010 | Agnew et al. |
| 2010/0114309 | A1 | 5/2010 | De et al. |
| 2010/0119580 | A1 | 5/2010 | Guo et al. |
| 2010/0137981 | A1 | 6/2010 | Silvestrini et al. |
| 2010/0161040 | A1 | 6/2010 | Braido et al. |
| 2010/0168644 | A1 | 7/2010 | Brown |
| 2010/0168839 | A1 | 7/2010 | Braido et al. |
| 2010/0185138 | A1 | 7/2010 | Yaron et al. |
| 2010/0185277 | A1 | 7/2010 | Braido et al. |
| 2010/0234793 | A1 | 9/2010 | Dacey et al. |
| 2010/0241046 | A1 | 9/2010 | Pinchuk et al. |
| 2010/0241241 | A1 | 9/2010 | Mcknight et al. |
| 2010/0259748 | A1 | 10/2010 | Suzuki |
| 2011/0027579 | A1 | 2/2011 | Tate |
| 2011/0028918 | A1 | 2/2011 | Hartwell et al. |
| 2011/0066098 | A1 | 3/2011 | Stergiopulos |
| 2011/0098640 | A1 | 4/2011 | Horne et al. |
| 2011/0112620 | A1 | 5/2011 | Du |
| 2011/0118835 | A1 | 5/2011 | Silvestrini et al. |
| 2011/0196487 | A1 | 8/2011 | Badawi et al. |
| 2011/0244014 | A1 | 10/2011 | Williams et al. |
| 2011/0257738 | A1 | 10/2011 | Corbett et al. |
| 2011/0270388 | A9 | 11/2011 | Stevens |
| 2011/0275912 | A1 | 11/2011 | Boyden et al. |
| 2011/0276128 | A1 | 11/2011 | Cao et al. |
| 2011/0282440 | A1 | 11/2011 | Cao et al. |
| 2011/0288635 | A1 | 11/2011 | Miller et al. |
| 2012/0035525 | A1 | 2/2012 | Silvestrini |
| 2012/0089073 | A1 | 4/2012 | Cunningham, Jr. |
| 2012/0123315 | A1 | 5/2012 | Horvath et al. |
| 2012/0123317 | A1 | 5/2012 | Horvath et al. |
| 2012/0141914 | A1 | 6/2012 | Namba et al. |
| 2012/0165720 | A1 | 6/2012 | Horvath et al. |
| 2012/0197175 | A1 | 8/2012 | Horvath et al. |
| 2012/0253453 | A1 | 10/2012 | Bruchman et al. |
| 2012/0310137 | A1 | 12/2012 | Silvestrini |
| 2012/0323315 | A1 | 12/2012 | Bruchman et al. |
| 2013/0046379 | A1 | 2/2013 | Paolitto et al. |
| 2013/0131577 | A1 | 5/2013 | Bronstein et al. |
| 2013/0158381 | A1 | 6/2013 | Rickard |
| 2013/0184810 | A1 | 7/2013 | Hall et al. |
| 2013/0190868 | A1 | 7/2013 | Kahook et al. |
| 2013/0211314 | A1 | 8/2013 | Venkatraman et al. |
| 2013/0218081 | A1 | 8/2013 | Roth |
| 2013/0226330 | A1 | 8/2013 | Sopori et al. |
| 2013/0274691 | A1 | 10/2013 | De Juan, Jr. et al. |
| 2013/0317413 | A1 | 11/2013 | Field et al. |
| 2013/0325024 | A1 | 12/2013 | Nissan et al. |
| 2013/0325111 | A1 | 12/2013 | Campbell et al. |
| 2014/0012371 | A1 | 1/2014 | Li |
| 2014/0031927 | A1 | 1/2014 | Bruchman et al. |
| 2014/0039468 | A1 | 2/2014 | Dunn |
| 2014/0107776 | A1 | 4/2014 | Williamson et al. |
| 2014/0114226 | A1 | 4/2014 | Snyder et al. |
| 2014/0128960 | A1 | 5/2014 | Greenslet et al. |
| 2014/0154321 | A1 | 6/2014 | Ashton |
| 2014/0170204 | A1 | 6/2014 | Desai et al. |
| 2014/0186420 | A1 | 7/2014 | Utkhede et al. |
| 2014/0214158 | A1 | 7/2014 | Board et al. |
| 2014/0236067 | A1 | 8/2014 | Horvath et al. |
| 2014/0236068 | A1 | 8/2014 | Van et al. |
| 2014/0243729 | A1 | 8/2014 | Rynerson |
| 2014/0343475 | A1 | 11/2014 | Smedley et al. |
| 2014/0343476 | A1 | 11/2014 | Penhasi |
| 2014/0358224 | A1 | 12/2014 | Tegels et al. |
| 2015/0005689 | A1 | 1/2015 | Horvath et al. |
| 2015/0057595 | A1 | 2/2015 | Gunn et al. |
| 2015/0119980 | A1 | 4/2015 | Beith et al. |
| 2015/0224200 | A1 | 8/2015 | De Juan, Jr. et al. |
| 2015/0224231 | A1 | 8/2015 | Bruchman et al. |
| 2015/0320975 | A1 | 11/2015 | Simpson et al. |
| 2015/0342875 | A1 | 12/2015 | Haffner |
| 2015/0374545 | A1 | 12/2015 | Horvath et al. |
| 2016/0000602 | A1 | 1/2016 | Meng et al. |
| 2016/0015516 | A1 | 1/2016 | Bernstein et al. |
| 2016/0038412 | A1 | 2/2016 | Guo et al. |
| 2016/0058615 | A1 | 3/2016 | Camras et al. |
| 2016/0058616 | A1 | 3/2016 | Camras et al. |
| 2016/0067032 | A1 | 3/2016 | Soletti et al. |
| 2016/0067093 | A1 | 3/2016 | Johnson et al. |
| 2016/0100939 | A1 | 4/2016 | Armstrong et al. |
| 2016/0153591 | A1 | 6/2016 | Fonfara et al. |
| 2016/0242962 | A1 | 8/2016 | Torello et al. |
| 2016/0245432 | A1 | 8/2016 | Fonfara et al. |
| 2016/0256321 | A1 | 9/2016 | Horvath et al. |
| 2016/0256382 | A1 | 9/2016 | Shi et al. |
| 2016/0270958 | A1 | 9/2016 | De et al. |
| 2016/0287513 | A1 | 10/2016 | Rakic et al. |
| 2016/0296322 | A1 | 10/2016 | Edelman et al. |
| 2016/0302965 | A1 | 10/2016 | Erickson et al. |
| 2016/0302967 | A1 | 10/2016 | Ahn |
| 2016/0331528 | A1 | 11/2016 | Parker et al. |
| 2016/0374856 | A1 | 12/2016 | Pinchuk et al. |
| 2017/0000610 | A1 | 1/2017 | Eppihimer et al. |
| 2017/0014227 | A1 | 1/2017 | Boden et al. |
| 2017/0020731 | A1 * | 1/2017 | Baerveldt ........... A61M 27/002 |
| 2017/0071729 | A1 | 3/2017 | Wrobel |
| 2017/0079779 | A1 | 3/2017 | Tabor |
| 2017/0079782 | A1 | 3/2017 | Beith |
| 2017/0141423 | A1 | 5/2017 | Okada et al. |
| 2017/0156854 | A1 | 6/2017 | Hammer |
| 2017/0172794 | A1 | 6/2017 | Varner et al. |
| 2017/0189175 | A1 | 7/2017 | Justino et al. |
| 2017/0245989 | A1 | 8/2017 | Bluestein et al. |
| 2017/0252156 | A1 | 9/2017 | Bernstein et al. |
| 2017/0296783 | A1 | 10/2017 | Connolly et al. |
| 2017/0367888 | A1 | 12/2017 | Brown |
| 2018/0028361 | A1 | 2/2018 | Haffner et al. |
| 2018/0049872 | A1 | 2/2018 | Bennett |
| 2018/0071143 | A1 | 3/2018 | Silvestrini et al. |
| 2018/0110650 | A1 | 4/2018 | Da Silva Curiel et al. |

(56) References Cited

U.S. PATENT DOCUMENTS

| | | | |
|---|---|---|---|
| 2018/0125632 | A1 | 5/2018 | Cully et al. |
| 2018/0126134 | A1 | 5/2018 | Cully et al. |
| 2018/0133002 | A1 | 5/2018 | Yi et al. |
| 2018/0133149 | A1 | 5/2018 | Zilberman |
| 2018/0177592 | A1 | 6/2018 | Benichou et al. |
| 2018/0185151 | A1 | 7/2018 | Bishop et al. |
| 2018/0263718 | A1 | 9/2018 | Griffiths et al. |
| 2018/0263775 | A1 | 9/2018 | Shah |
| 2018/0263817 | A1 | 9/2018 | Roeber et al. |
| 2018/0263818 | A1 | 9/2018 | Roeber et al. |
| 2018/0263819 | A1 | 9/2018 | Roeber et al. |
| 2018/0303752 | A1 | 10/2018 | Haffner |
| 2018/0325732 | A1 | 11/2018 | Burns et al. |
| 2018/0344457 | A1 | 12/2018 | Gross et al. |
| 2018/0344526 | A1 | 12/2018 | Pinchuk |
| 2019/0000673 | A1 | 1/2019 | Fjield et al. |
| 2019/0015191 | A1 | 1/2019 | Berdajs |
| 2019/0046696 | A1 | 2/2019 | Parikh et al. |
| 2019/0091014 | A1 | 3/2019 | Arcaro et al. |
| 2019/0091015 | A1 | 3/2019 | Dienno et al. |
| 2019/0105199 | A1 | 4/2019 | Ahmed et al. |
| 2019/0125529 | A1 | 5/2019 | Colavito et al. |
| 2019/0125530 | A1 | 5/2019 | Arcaro et al. |
| 2019/0125531 | A1 | 5/2019 | Bennett et al. |
| 2019/0133826 | A1 | 5/2019 | Horvath et al. |
| 2019/0167475 | A1 | 6/2019 | Horvath et al. |
| 2019/0224047 | A1 | 7/2019 | Kao et al. |
| 2019/0282360 | A1 | 9/2019 | Colavito et al. |
| 2019/0298572 | A1 | 10/2019 | Chu |
| 2019/0343617 | A1 | 11/2019 | Sobrino-Serrano et al. |
| 2019/0365531 | A1 | 12/2019 | Beith |
| 2020/0113681 | A1 | 4/2020 | Armstrong et al. |
| 2020/0121454 | A1 | 4/2020 | Spence |
| 2020/0188114 | A1 | 6/2020 | Radspinner et al. |
| 2020/0188147 | A1 | 6/2020 | Throckmorton et al. |
| 2020/0214886 | A1 | 7/2020 | Gutierrez |
| 2020/0214887 | A1 | 7/2020 | Gutierrez |
| 2020/0229977 | A1 | 7/2020 | Mixter et al. |
| 2020/0330377 | A1 | 10/2020 | Banerjee et al. |
| 2020/0337897 | A1 | 10/2020 | Sacherman et al. |
| 2021/0205130 | A1 | 7/2021 | Campbell et al. |
| 2021/0315806 | A1 | 10/2021 | Haffner |
| 2021/0322217 | A1 | 10/2021 | Roeber et al. |
| 2021/0346197 | A1 | 11/2021 | Roeber et al. |
| 2022/0080049 | A1 | 3/2022 | Garcia et al. |
| 2022/0331162 | A1 | 10/2022 | Roeber et al. |
| 2022/0354996 | A1 | 11/2022 | Engman et al. |
| 2022/0378611 | A1 | 12/2022 | Conia et al. |
| 2022/0395397 | A1 | 12/2022 | Chu |
| 2023/0054622 | A1 | 2/2023 | Roeber et al. |
| 2023/0117758 | A1 | 4/2023 | Roeber et al. |
| 2023/0142430 | A1 | 5/2023 | Towler et al. |
| 2023/0142433 | A1 | 5/2023 | Towler et al. |
| 2024/0041645 | A1 | 2/2024 | Conia et al. |

FOREIGN PATENT DOCUMENTS

| | | | |
|---|---|---|---|
| AU | 2015266850 | A1 | 12/2016 |
| AU | 2020201236 | A1 | 3/2020 |
| AU | 2017439185 | A1 | 5/2020 |
| AU | 2021218010 | A1 | 9/2021 |
| CA | 2502761 | A1 | 4/1997 |
| CA | 2974600 | A1 | 10/2015 |
| CA | 2950187 | A1 | 12/2015 |
| CN | 1208602 | A | 2/1999 |
| CN | 2414757 | Y | 1/2001 |
| CN | 1285724 | A | 2/2001 |
| CN | 1425826 | A | 6/2003 |
| CN | 1592640 | A | 3/2005 |
| CN | 1976732 | A | 6/2007 |
| CN | 101965211 | A | 2/2011 |
| CN | 202619978 | U | 12/2012 |
| CN | 103179927 | A | 6/2013 |
| CN | 103619366 | A | 3/2014 |
| CN | 104000684 | A | 8/2014 |
| CN | 104114201 | A | 10/2014 |
| CN | 104168863 | A | 11/2014 |
| CN | 105377202 | A | 3/2016 |
| CN | 105579001 | A | 5/2016 |
| CN | 205198254 | U | 5/2016 |
| CN | 107613917 | A | 1/2018 |
| EP | 2226624 | A1 | 9/2010 |
| EP | 2472297 | A1 | 7/2012 |
| EP | 2349147 | B1 | 3/2015 |
| EP | 2958530 | A1 | 12/2015 |
| EP | 3148491 | A1 | 4/2017 |
| EP | 3148491 | B1 | 7/2020 |
| EP | 3677229 | A1 | 7/2020 |
| EP | 3773377 | A1 | 2/2021 |
| GB | 2513194 | A | 10/2014 |
| JP | 08-117267 | A | 5/1996 |
| JP | 11-505159 | A | 5/1999 |
| JP | 2000-513248 | A | 10/2000 |
| JP | 2002-521145 | A | 7/2002 |
| JP | 2003-301948 | A | 10/2003 |
| JP | 2005-500101 | A | 1/2005 |
| JP | 2005-121438 | A | 5/2005 |
| JP | 2005-294016 | A | 10/2005 |
| JP | 2007-521125 | | 8/2007 |
| JP | 2008-101926 | A | 5/2008 |
| JP | 2010-540079 | A | 12/2010 |
| JP | 2011-504127 | A | 2/2011 |
| JP | 2011-507631 | A | 3/2011 |
| JP | 2012-504031 | A | 2/2012 |
| JP | 2012-164647 | A | 8/2012 |
| JP | 2013-009982 | A | 1/2013 |
| JP | 2014-517720 | A | 7/2014 |
| JP | 2014-199348 | A | 10/2014 |
| JP | 2014-239034 | A | 12/2014 |
| JP | 2015-039515 | A | 3/2015 |
| JP | 2015-175815 | A | 10/2015 |
| JP | 2016-137278 | A | 8/2016 |
| JP | 2017-517363 | A | 6/2017 |
| JP | 6655610 | B2 | 2/2020 |
| JP | 2020-509892 | A | 4/2020 |
| JP | 2020-075162 | A | 5/2020 |
| JP | 6872650 | B2 | 5/2021 |
| JP | 2021-112598 | A | 8/2021 |
| KR | 10-2008-0020259 | A | 3/2008 |
| KR | 10-2016-0026107 | A | 3/2016 |
| WO | 2001/066037 | A2 | 9/2001 |
| WO | 02/00318 | A1 | 1/2002 |
| WO | 2002/100318 | A2 | 12/2002 |
| WO | 2003/007795 | A2 | 1/2003 |
| WO | 03/15659 | A2 | 2/2003 |
| WO | 2005/076973 | A2 | 8/2005 |
| WO | 2007/100408 | A2 | 9/2007 |
| WO | 2008/030246 | A2 | 3/2008 |
| WO | 2008/030951 | A2 | 3/2008 |
| WO | 2008/133852 | A1 | 11/2008 |
| WO | 2009/042196 | A2 | 4/2009 |
| WO | 2009/137785 | A2 | 11/2009 |
| WO | 2010/037141 | A1 | 4/2010 |
| WO | 2011/147849 | A1 | 12/2011 |
| WO | 2012/018779 | A2 | 2/2012 |
| WO | 2012/135603 | A2 | 10/2012 |
| WO | 2012/142318 | A1 | 10/2012 |
| WO | 2013/090006 | A1 | 6/2013 |
| WO | 2013/096854 | A3 | 8/2013 |
| WO | 2014/028725 | A1 | 2/2014 |
| WO | 2014/130574 | A1 | 8/2014 |
| WO | 2014/145811 | A1 | 9/2014 |
| WO | 2015/064312 | A1 | 5/2015 |
| WO | 2015/065646 | A1 | 5/2015 |
| WO | 2015/085234 | A1 | 6/2015 |
| WO | 2015/126332 | A1 | 8/2015 |
| WO | 2015/184173 | A1 | 12/2015 |
| WO | 2016/033270 | A1 | 3/2016 |
| WO | 2016/168686 | A1 | 10/2016 |
| WO | 2016/196841 | A1 | 12/2016 |
| WO | 2017/156293 | A1 | 9/2017 |
| WO | 2017/176886 | A1 | 10/2017 |
| WO | 2018/150392 | A1 | 8/2018 |
| WO | 2018/170429 | A1 | 9/2018 |

(56) References Cited

FOREIGN PATENT DOCUMENTS

| | | | |
|---|---|---|---|
| WO | 2018/170433 | A1 | 9/2018 |
| WO | 2018/187714 | A1 | 10/2018 |
| WO | 2019/018807 | A1 | 1/2019 |
| WO | 2019/094004 | A1 | 5/2019 |
| WO | 2019/154927 | A1 | 8/2019 |
| WO | 2020/047221 | A1 | 3/2020 |
| WO | 2020/047222 | A1 | 3/2020 |
| WO | 2020/223525 | A1 | 11/2020 |

OTHER PUBLICATIONS

International Preliminary Report on Patenlability received for PCT Patent Application No. PCT/US2018/022929, mailed on Sep. 26, 2019, 9 pages.
International Preliminary Report on Patentability received for PCT Patent Application No. PCT/US18/22922, mailed on Sep. 26, 2019, 9 pages.
International Preliminary Report on Patentability received for PCT Patent Application No. PCT/US18/22933, mailed on Sep. 26, 2019, 9 pages.
International Preliminary Report on Patentability received for PCT Patent Application No. PCT/US19/48759, mailed on Mar. 11, 2021, 12 pages.
International Preliminary Report on Patentability received for PCT Patent Application No. PCT/US19/48760, mailed on Mar. 11, 2021, 9 pages.
International Preliminary Report on Patentability received for PCT Patent Application No. PCT/US2015/055348, dated Apr. 27, 2017, 18 pages.
International Preliminary Report on Patentability received for PCT Patent Application No. PCT/US2019/065890, mailed on Jun. 24, 2021, 8 pages.
International Preliminary Report on Patentability received for PCT Patent Application No. PCT/US2022/031305, mailed on Dec. 7, 2023, 18 pages.
International Preliminary Report on Patentability received for PCT Patent Application No. PCT/US2023/010660, mailed on Jul. 25, 2024, 10 pages.
International Preliminary Report on Patentability received for PCT Patent Application No. PCT/US22/48960, mailed on May 16, 2024, 10 pages.
International Preliminary Report on Patentability received for PCT Patent Application No. PCT/US22/48971, mailed on May 16, 2024, 13 pages.
International Search Report and Written Opinion received for PCT Patent Application No. PCT/US18/22922, mailed on Jul. 23, 2018, 12 pages.
International Search Report and Written Opinion received for PCT Patent Application No. PCT/US18/22929, mailed on Jun. 28, 2018, 12 pages.
International Search Report and Written Opinion received for PCT Patent Application No. PCT/US18/22933, mailed on Jul. 3, 2018, 12 pages.
International Search Report and Written Opinion received for PCT Patent Application No. PCT/US19/48759, mailed on Feb. 12, 2020, 16 pages.
International Search Report and Written Opinion received for PCT Patent Application No. PCT/US19/48760, mailed on Dec. 3, 2019, 11 pages.
International Search Report and Written Opinion received for PCT Patent Application No. PCT/US2015/055348, mailed on Apr. 11, 2016, 23 pages.
International Search Report and Written Opinion received for PCT Patent Application No. PCT/US2018/050771, mailed on Feb. 25, 2019, 16 pages.
International Search Report and Written Opinion received for PCT Patent Application No. PCT/US2019/065890, dated Mar. 18, 2020, 9 pages.
International Search Report and Written Opinion received for PCT Patent Application No. PCT/US2022/031305, mailed on Nov. 7, 2022, 26 pages.
International Search Report and Written Opinion received for PCT Patent Application No. PCT/US2022/048960, mailed on Mar. 2, 2023, 17 pages.
International Search Report and Written Opinion received for PCT Patent Application No. PCT/US2022/048971, mailed on Apr. 24, 2023, 19 pages.
International Search Report and Written Opinion received for PCT Patent Application No. PCT/US2023/029614, mailed on Nov. 10, 2023, 13 pages.
Invitation to pay additional fees received for PCT Patent Application No. PCT/US19/48759, mailed on Dec. 11, 2019, 10 pages.
Invitation to pay additional fees received for PCT Patent Application No. PCT/US22/31305, mailed on Sep. 15, 2022, 23 pages.
Invitation to pay additional fees received for PCT Patent Application No. PCT/US22/48971, mailed on Mar. 2, 2023, 13 pages.
Lee et al., "Pig eye trabeculectomy—a wet-lab teaching model," Eye, vol. 20, Jan. 28, 2005, pp. 32-37.
Office Action received for Chinese Patent Application No. 202110966241.1, mailed on May 15, 2024, 11 pages (5 pages of English Translation and 6 pages of Original Document).
Shastri, V et al. Non-Degradable Biocompatible Polymers in Medicine: Past, Present, and Future. Current Pharmaceutical Biotechnology, vol. 4, No. 5, 2003, pp. 331-337 [online], [retrieved on Nov. 8, 2023], Retrieved from the Internet <URL: https://pubmed.ncbi.nlm.nih.gov/14529423/> (Year: 2003).
Tang, H., Zhang, Y., Wang, F., Zhang, H., & Guo, Y. (2016). Long-term stability of polytetrafluoroethylene (PTFE) hollow fiber membranes for CO2 capture. Energy & Fuels, 30(1), 492-503. (Year: 2019).
Wadhawan, A et. al. Gore-tex® versus resolut adapt® GTR membranes with perioglas® in periodontal regeneration. Contemp. Clin. Dent., vol. 3, No. 4, Oct.-Dec. 2012, pp. 406-411 [online], [retrieved on Nov. 8, 2023], Retrieved from the Internet <URL: https://www.ncbi.nlm.nih.gov/pmc/articles/PMC3636825/> (Year: 2012).
"The Ahmed Giaucoma Valve Model FP7," New World Medical, Inc., Part #50-0088 Rev C, URL: hpps://www.newworldmedical.com/wp-content/uploads/2020/07/AGV-FP7-IFU-50-0088-Rev-C.pdf, Nov. 2019, pp. 1-28.
Ando et al., Ten-year experience with handmade trileaflet polytetrafluoroethylene valved conduit used for pulmonary reconstruction. The Journal of Thoracic and Cardiovascular Surgery, Jan. 2009, vol. 137, No. 1, pp. 124-131.
Gedde et al., "Treatment Outcomes in the Tube Versus Trabeculectomy (TVT) Study After Five Years of Follow-up", Am J Ophthalmol., vol. 153, No. 5, 2012, pp. 789-803.
Han, et al. "Membrane-tube-type glaucoma shunt device for refractory glaucoma surgery", Glaucoma, Graefes Arch Clin Exp Opthalmol, DOI 10, 1007/s00417-016-3510-z. Springer-Verlag Berlin Heidelberg 2016.
International Search Report and Written Opinion received for PCT Patent Application No. PCT/US2023/010660, mailed on May 24, 2023, 17 pages.
Kahook et al., "Location of glaucoma drainage devices relative to the optic nerve," British Journal of Ophthalmol, vol. 90, No. 8, Aug. 2006, pp. 1010-1013.
Karthikeyan et al., "The concept of ocular inserts as drug delivery systems: An overview", Asian Journal of Pharmaceutics, vol. 2, No. 4, 2008, pp. 192-200.
Lee et al., "Aqueous-Venous Shunt for Glaucoma A Further Report", Arch Opthalmol, vol. 99, 1981, pp. 2007-2012.
Lee et al., "Aqueous-Venous Shunt in The Rabbit Eye: A Long-Term Follow-Up", Trans. Soc. Ophthal. Sin., vol. 8, 1969, pp. 7-24.
Lee et al., "Aqueous-Venus Shunt for Glaucoma: Report on 15 cases", AnnalOphthal, Oct. 1974, pp. 1083-1088.
Lee et al., "Effect of an Aqueous-Venous Shunt In The Monkey Eye", Canad. J. Ophthal., 3:22, 1968, pp. 22-27.
Lee et al., "Effect of aqueous-venous shunt on rabbit eyes", Inivestigative Ophthalmology, vol. 5, No. 3, 1996, pp. 304-311.
Lee et al., "Glaucoma Microsurgery Aqueous-Venous Shunt Procedure", International Surgery, vol. 57, No. 1, Jan. 1972, pp. 37-41.

(56) References Cited

OTHER PUBLICATIONS

McMenamin et al., "Normal anatomy of the aqueous humour outflow system in the domestic pig eye," Journal of Anatomy, vol. 178, Oct. 1991, pp. 65-77.
Miyazaki, et al., Expanded polytetrafluoroethylene conduits and patches with bulging sinuses and fan-shaped valves in right ventricular outflow tract reconstruction: Multicneter study in Japan. The Journal of Thoracic and Cardiovascula Surgery, Nov. 2011, vol. 142, No. 5, pp. 1122-1129.
Miyazaki, et al., Expanded polytetrafluoroethylene valved conduit and patch with bulging sinuses in right ventricular outflow tract reconstruction. The Journal of Thoracic and Cardiovascular Surgery, Aug. 2007, vol. 134, No. 2, pp. 327-332.
Mohammadi et al., "Sheep practice eye for ophthalmic surgery training in skills laboratory," Journal of Cataract and Refractive Surgery, vol. 37, No. 6, Jun. 2011, pp. 987-991.
Ootaki et al., Medium-term outcomes after implantation of expanded polytetrafluoroethylene valved conduit. The Annals of Thoracic Surgery, 2018; 105 (3), pp. 843-850.
Palioura S. et al., "Role of steroids in the treatment of bacterial keratitis," Clinical Ophthalmology. vol. 10, Jan. 27, 2016, pp. 179-186.
Plemel et al., "Tube shunt surgery in pig eyes: a wet lab teaching model," Canadian Journal of Ophthalmology, vol. 54, Issue 5, Oct. 2019, pp. 585-589.
Rese et al., "Sustained drug delivery in glaucoma", Current Opinion in Ophthalmology, vol. 25, No. 2, 2014, pp. 112-117.
Shinkawa et al., Valved polytetrafluoroethylene conduits for right ventricular outflow tract reconstruction. The Annals of Thoracic Surgery. Jul. 2015; 100(1), pp. 129-137.
Stevenson et al., "Reservoir-Based Drug Delivery Systems Utilizing Microtechnology", Advanced Drug Delivery Reviews, vol. 64, No. 14, 2012, pp. 1590-1602.
Understanding Your Heart Valve. Medtronic USA, Inc., 2006. Pamphlet.
Yamagishi et al. Outflow reconstruction of tetralogy of fallot using a Gore-Tex valve. The Anais of Thoracic Surgery, Dec. 1993; 56(6), pp. 1414-1417.
Exam Report issued in Indian Patent Application No. 202417056731, dated May 11, 2026.
Korean-language Office Action issued in Korean Application No. 10-2024-7026960 dated Jun. 22, 2026 with English translation (23 pages).

* cited by examiner

200

200

200

BIOLOGICAL FLUID DRAINAGE DEVICES, SYSTEMS, AND METHODS

CROSS-REFERENCE TO RELATED APPLICATION

This application claims the benefit of U.S. Provisional Application No. 63/298,854, filed Jan. 12, 2022, which is incorporated herein by reference in its entirety for all purposes.

FIELD

The present disclosure relates generally to apparatuses, systems, and methods for draining biological fluid and diverting the fluid to be reabsorbed elsewhere in the body. More specifically, the disclosure relates to apparatuses, systems, and methods for draining aqueous humor from the anterior chamber of a patient's eye such that it may be reabsorbed by the body.

BACKGROUND

Various medical interventions involve evacuating excess biological fluid from one portion of the body and redirecting it to another location of the body where it may be reabsorbed. In certain instances, this evacuation is achieved via minimally invasive procedures such as endoscopic third ventriculostomy (ETV) and choroid plexus cauterization procedure (CPC). In other instances, this evacuation is performed post-operatively via implantable medical devices, such as a shunt. Proven useful in various medical procedures, shunts of different forms have been employed as treatment for numerous diseases, such as hydrocephalus and glaucoma.

Without treatment, excessive biological fluid may lead to unhealthy pressure buildups. For instance, glaucoma is a progressive eye disease characterized by elevated intraocular pressure. Aqueous humor is a fluid that fills the anterior chamber of the eye and contributes to intraocular pressure or intraocular fluid pressure. This increase in intraocular pressure is usually caused by an insufficient amount of aqueous humor absorbed by the body. In some cases, the aqueous humor is not absorbed quickly enough or even not absorbed at all, while in other cases, the aqueous humor is additionally or alternatively produced too quickly. Elevated intraocular pressure is associated with gradual and sometimes permanent loss of vision in the affected eye.

Many attempts have been made to treat glaucoma. However, some conventional devices are relatively bulky and lack flexibility, compliance, and device/tissue attachment required to avoid relative motion between the device and the surrounding tissue. Such movement may result in continued stimulation of the surrounding tissue, causing irritation at the implantation site. Irritation, in turn, may lead to increased chronic inflammatory tissue response, excessive scarring at the device site, and increased risk of device erosion through conjunctival and endophthalmitis. Scar tissue effectively prevents resorption of aqueous humor without erosion. These complications may prevent the device from functioning properly. The result is a gradual rise in intraocular pressure and progression of glaucoma.

FIGS. 1A and 1B illustrate a glaucoma drainage device 100 as known in the art. The device 100 includes a plate body 102 which defines a surface over which the drained fluid (aqueous humor) is directed to flow, and a drainage tube 104 which directs the fluid (aqueous humor) to flow over the surface of the plate body. The plate body 102 has a maximum thickness "t1" which in the example shown is 2.1 mm, and is made of medical-grade silicone which lacks flexibility to conform to the curvature of the eye when implanted. As such, the plate body 102 has a curvature (defined by the broken line C-C in FIG. 1B) which is preformed (that is, before implantation) to approximate the curvature of the surface of the eye. The curvature C-C is fixed and is the same for all glaucoma drainage devices, thus in some cases fail to accommodate the unique curvature of each patient's eye.

Reference is made to FIGS. 1C through 1H with regard to an exemplary procedure of implanting the glaucoma drainage device 100 in the eye tissue of the patient. In FIG. 1C, a fornix-based incision 17 is made through a conjunctiva 13 of the patient's eye 10 using a scalpel. In FIG. 1D, the plate body 102 of the glaucoma drainage device 100 is inserted into a pocket of the tissue made by the incision 17 until the entire plate body 102 is disposed inside the tissue pocket and a portion of the drainage tube 104 remains outside the pocket. In FIG. 1E, the portion of the drainage tube 104 which is exposed outside the pocket is trimmed to permit a 2-3 mm insertion of the tube 104 into the anterior chamber (AC). In FIG. 1F, a paracentesis is performed, and the AC is entered with a sharp needle 19, for example a 23-gauge needle, to create a needle track, parallel to the iris, while the trimmed end of the drainage tube 104 remains outside the eye tissue. In FIG. 1G, the drainage tube 104 is inserted approximately 2-3 mm into the AC through the needle track created in FIG. 1F. In FIG. 1H, the exposed portion of the drainage tube 104 which remains external to the eye tissue is then covered with a patch graft or coverage 106. The patch graft or coverage 106 may be a piece of preserved sclera, donor sclera, pericardium, cornea, or any other suitable patch graft material. The patch graft or coverage 106 is then sutured into place and the conjunctiva 13 is closed.

In the prior-art device 100, the plate body 102 has a structure that is stiff to allow the user to hold any part of the plate body 102 using tools such medical tweezers, hemostats, or any other suitable medical tool to hold the plate body 102, and the user can push the plate body 102 into the tissue pocket made by the incision 17 as shown in FIG. 1D while holding the plate body 102 with the medical tool. As such, the prior-art device 100 relies upon the stiffness of the plate body 102 for implantation and the implantation method as described in FIG. 1D would not work for a thinner material that is highly flexible and collapsible (for example foldable, deformable, bendable, or crumplable, i.e. capable of being crumpled), because the device would be difficult, if not impossible, to be inserted by the user via the pushing method because such pushing motion would cause the device to be disposed in an improper position or to assume a malformed arrangement of components. Likewise, the prior-art device 100 relies upon a slippery or low-friction surface of the device to facilitate the pushing insertion method, and thus, any device with a higher surface friction would experience resistance against the pushing motion which would likely lead to deformation of the device during implantation, caused by the high friction which collapses (e.g., flexes, folds, buckles, deforms, or crumples) the device.

Additionally, the device is desirable to have a sufficiently thin configuration because the thinness provides a lower profile that minimizes an adverse tissue response. Thus there is a need for a glaucoma drainage device with a thin and flexible body that can be inserted into the eye tissue while avoiding collapse and mispositioning of the device in situ and that overcomes the aforementioned limitations of the prior art.

SUMMARY

Disclosed herein are drainage devices for draining a biological fluid from an eye to a tissue surrounding the eye, as well as methods for forming the drainage device that is implantable at least in part within a tissue of an eye and methods for treating a glaucoma using the drainage device.

According to one example ("Example 1"), a drainage device is configured to drain a biological fluid from an eye to a tissue external to the eye, the drainage device is implantable at least in part within a tissue of the eye, and the drainage device includes: a collapsible body portion defining a reservoir and a conduit having a first end fluidly coupled with the reservoir and a second end insertable into the eye to facilitate a drainage of the biological fluid into the conduit. The collapsible body portion, when collapsed, includes a deformation of the body portion from a first planar state to a second nonplanar state. In situ, the second nonplanar state is at least one of a folded state, a deformed state, a bent state, or a crumpled state. During implantation, the collapsible body portion includes at least one temporary reinforcement element that maintains the collapsible body portion in the first planar state.

According to one example ("Example 2") further to Example 1, the collapsible body portion includes a delivery member conduit formed on an outer surface of the collapsible body portion. The temporary reinforcement element is at least one flexible wire partially received within the delivery member conduit.

According to one example ("Example 3") further to Example 2, the delivery member conduit is positioned along a periphery of the reservoir or a periphery of the body member.

According to one example ("Example 4") further to Example 3, the delivery member conduit is positioned between the periphery of the reservoir and the periphery of the body member.

According to one example ("Example 5") further to Example 3 or 4, the delivery member conduit includes a first opening configured to receive a first temporary reinforcement element and a second opening is configured to receive a second temporary reinforcement element.

According to one example ("Example 6") further to Example 5, the first and second temporary reinforcement elements are configured to overlap within the delivery member conduit.

According to one example ("Example 7") further to Example 1, the temporary reinforcement element is attached to an outer surface of the collapsible body portion, the temporary reinforcement element including an adsorbable material that is adsorbable into the tissue of the eye in which the drainage device is implanted.

According to one example ("Example 8") further to Example 1, the reservoir is able to receive a portion of the temporary reinforcement element via the conduit to facilitate delivery of the drainage device to be implanted within the tissue of the eye, the temporary reinforcement element being retractable from the reservoir after the drainage device is implanted.

According to one example ("Example 9") further to any preceding Example, the collapsible body portion is made of a microporous material.

According to one example ("Example 10") further to Example 9, the microporous material is expanded polytetrafluoroethylene (ePTFE).

According to one example ("Example 11") further to Example 9 or 10, the microporous material includes a plurality of subsections having various pore sizes.

According to one example ("Example 12") further to Example 11, the microporous material facilitates absorption of the biological fluid from the reservoir to be released to an outer environment surrounding the collapsible body portion.

According to one example ("Example 13") further to Example 12, the microporous material reduces tissue ingrowth from the outer environment into the reservoir.

According to one example ("Example 14") further to any preceding Example, the first planar state is defined by a curved plane corresponding to a curvature of the eye.

According to one example ("Example 15") further to any preceding Example, the collapsible body portion includes a material that is sufficiently flexible to deform in response to a directional force being applied to the body portion during implantation of the drainage device.

According to one example ("Example 16") further to Example 15, the collapsible body portion deforms in response to an external frictional force caused by the tissue of the eye when applying the directional force to the body portion during implantation of the drainage device.

According to one example ("Example 17") further to any preceding Example, the collapsible body portion has a first length in an uncollapsed state in absence of an external force, a second length less than the first length in a collapsed state when the external force is applied, and a third length greater than the second length and less than the first length in a resting state after the external force is removed.

According to one example ("Example 18") further to Example 17, the third length is no greater than approximately 90% of the first length.

According to one example ("Example 19") further to any preceding Example, the collapsible body portion is formed by at least partially adhering a periphery of a first body layer to a periphery of a second body layer.

According to one example ("Example 20") further to any preceding Example, the collapsible body portion includes at least one suture hole configured to receive a suture to facilitate attaching the drainage device to the tissue of the eye.

According to one example ("Example 21") further to any preceding Example, the collapsible body portion further includes at least one marker to mark a position of the conduit along the body portion.

According to one example ("Example 22") further to any one of Examples 2-6, the delivery member is a flexible delivery wire including a nickel-titanium alloy.

According to one example ("Example 23") further to any preceding Example, the collapsible body portion has a thickness of no greater than about 0.5 mm around the reservoir when the reservoir is empty.

According to one example ("Example 24"), a drainage device is configured to drain a biological fluid from an eye to a tissue external to the eye, the drainage device is implantable at least in part within a tissue of the eye, and the drainage device includes: a collapsible body portion defining a reservoir and a retaining portion and a conduit having a first end fluidly coupled with the reservoir and a second end insertable into the eye to facilitate a drainage of the biological fluid into the conduit. The collapsible body portion, when collapsed, includes a deformation of the body portion from a first planar state to a second nonplanar state. In situ, the second nonplanar state is at least one of a folded state, a deformed state, a bent state, or a crumpled state. The retaining portion of the collapsible body portion is sized and positioned to convey a pulling force to the collapsible body portion to maintain the collapsible body portion in the first planar state during implantation.

According to one example ("Example 25") further to Example 24, the pulling force is supplied by a delivery member engaging the retaining portion.

According to one example ("Example 26") further to Example 25, the retaining portion is a pocket formed partially in the collapsible body portion, and the delivery member has a curved portion at a distal end which is partially received by the pocket.

According to one example ("Example 27") further to any one of Examples 24-26, the first planar state is defined by a curved plane corresponding to a curvature of the eye.

According to one example ("Example 28") further to any one of Examples 24-27, the collapsible body portion includes a material that is sufficiently flexible to deform in response to a directional force being applied to the body portion during implantation of the drainage device.

According to one example ("Example 29") further to Example 29, the collapsible body portion deforms in response to an external frictional force caused by the tissue of the eye when applying the directional force to the body portion during implantation of the drainage device.

According to one example ("Example 30") further to any one of Examples 24-29, the collapsible body portion has a first length in an uncollapsed state in absence of an external force, a second length less than the first length in a collapsed state when the external force is applied, and a third length greater than the second length and less than the first length in a resting state after the external force is removed.

According to one example ("Example 31") further to Example 30, the third length is no greater than approximately 90% of the first length.

According to one example ("Example 32") further to any one of Examples 24-31, the collapsible body portion is formed by at least partially adhering a periphery of a first body layer to a periphery of a second body layer.

According to one example ("Example 33") further to any one of Examples 24-32, the collapsible body portion includes at least one suture hole configured to receive a suture to facilitate attaching the drainage device to the tissue of the eye.

According to one example ("Example 34") further to any one of Examples 24-33, the collapsible body portion further includes at least one marker to mark a position of the conduit along the body portion.

According to one example ("Example 35") further to Example 25 or 26, the delivery member is a flexible delivery wire including a nickel-titanium alloy.

According to one example ("Example 36") further to any one of Examples 24-35, the collapsible body portion has a thickness of no greater than about 0.5 mm around the reservoir when the reservoir is empty.

According to one example ("Example 37"), a method of forming a drainage device implantable at least in part within a tissue of an eye, includes: arranging one or more layers of material to form a collapsible body portion with a reservoir defined therein, the reservoir being configured to receive and accumulate biological fluid; and securing a conduit to the reservoir such that a first end of the conduit is fluidly coupled with the reservoir and a second end of the conduit is deliverable into the eye to facilitate a drainage of the biological fluid into the conduit.

According to one example ("Example 38") further to Example 37, the collapsible body portion includes a material that is sufficiently flexible to deform in response to a directional force being applied to the body portion during implantation of the drainage device.

According to one example ("Example 39") further to Example 38, the collapsible body portion includes a material that is sufficiently flexible to deform via an external frictional force caused by applying the directional force to the body portion during implantation of the drainage device.

According to one example ("Example 40") further to Example 38 or 39, the collapsible body portion has a recovery force less than a minimal force required to at least temporarily overcome a force exerted by an entrance of the tissue of the eye for the body portion to be inserted at least partially into the tissue of the eye.

According to one example ("Example 41") further to any one of Examples 37-40, the collapsible body portion has a first length in an uncollapsed state in absence of an external force, a second length less than the first length in a collapsed state when the external force is applied, and a third length greater than the second length and less than the first length in a resting state after the external force is removed.

According to one example ("Example 42") further to Example 41, the third length is no greater than approximately 90% of the first length.

According to one example ("Example 43") further to any one of Examples 37-42, the one or more layers of material include a first body layer and a second body layer. The method further includes at least partially adhering a periphery of the first body layer to a periphery of the second body layer to form the collapsible body portion.

According to one example ("Example 44") further to any one of Examples 37-43, the method further includes forming at least one suture hole on the collapsible body portion that is configured to receive a suture to facilitate attaching the drainage device to the tissue of the eye.

According to one example ("Example 45") further to any one of Examples 37-44, the method further includes forming at least one marker on the collapsible body portion that is configured to mark a position of the conduit along the body portion.

According to one example ("Example 46") further to any one of Examples 37-45, the method further includes: providing at least one support member to facilitate delivery of the drainage device to be implanted within the tissue of the eye to be disposed in an uncollapsed state with a planar configuration, the at least one support member including an adsorbable material configured to adsorb into the tissue of the eye in which the drainage device is implanted; and attaching the at least one support member to an outer surface of the collapsible body portion.

According to one example ("Example 47") further to any one of Examples 37-45, the method further includes: inserting a portion of a delivery member into the reservoir via the conduit to facilitate delivery of the drainage device to be implanted within the tissue of the eye to be disposed in an uncollapsed state with a planar configuration. The delivery member is retractable from the reservoir after the drainage device is implanted.

According to one example ("Example 48") further to Example 46 or 47, the planar configuration is defined by a curved plane corresponding to a curvature of the eye.

According to one example ("Example 49") further to any one of Examples 37-48, the delivery member is a flexible delivery wire including a nickel-titanium alloy.

According to one example ("Example 50") further to any one of Examples 37-49, the collapsible body portion includes a microporous material.

According to one example ("Example 51") further to Example 50, the microporous material includes a plurality of subsections having various degrees of porosity.

According to one example ("Example 52") further to Example 50 or 51, the microporous material facilitates absorption of the biological fluid from the reservoir to be released to an outer environment surrounding the collapsible body portion.

According to one example ("Example 53") further to Example 52, the microporous material reduces tissue ingrowth from the outer environment into the reservoir.

According to one example ("Example 54") further to any one of Examples 37-46, the method further includes: forming a delivery member retaining portion on the collapsible body portion positioned outer to the reservoir and disconnected from the reservoir. The delivery member retaining portion is configured to at least partially receive a delivery member to facilitate delivery of the drainage device to the tissue of the eye.

According to one example ("Example 55") further to Example 54, the delivery member retaining portion is a pocket formed partially in the collapsible body portion, and the delivery member has a curved portion at a distal end which is at least partially receivable by the pocket.

According to one example ("Example 56") further to Example 54, the delivery member retaining portion is a delivery member conduit formed on an outer surface of the collapsible body portion, and the delivery member is at least one flexible wire partially receivable within the delivery member conduit.

According to one example ("Example 57") further to Example 56, the method further includes positioning the delivery member conduit along a periphery of the reservoir or a periphery of the body member.

According to one example ("Example 58") further to Example 57, the method further includes positioning the delivery member conduit between the periphery of the reservoir and the periphery of the body member.

According to one example ("Example 59") further to Example 57 or 58, the delivery member conduit includes a first opening configured to receive a first flexible wire and a second opening is configured to receive a second flexible wire.

According to one example ("Example 60") further to Example 59, the method further includes inserting the first flexible wire into the delivery member conduit via the first opening and inserting the second flexible wire into the delivery member conduit via the second opening such that the first flexible wire and the second flexible wire overlap within the delivery member conduit during delivery of the drainage device.

According to one example ("Example 61") further to any one of Examples 37-46, the collapsible body portion is configured to be delivered to the tissue of the eye in a folded configuration using a delivery member and subsequently unfolded to be implanted.

According to one example ("Example 62") further to any one of Examples 37-46, the collapsible body portion is configured to be delivered to the tissue of the eye in a wrapped configuration using a delivery member and subsequently unwrapped to be implanted.

According to one example ("Example 63") further to any one of Examples 37-62, the collapsible body portion has a thickness of no greater than about 0.5 mm around the reservoir when the reservoir is empty.

According to one example ("Example 64"), a method of treating a glaucoma using a drainage device includes: removably coupling at least a portion of a delivery member to a collapsible body portion of the drainage device, the collapsible body portion defining a reservoir disposed to receive and accumulate a biological fluid via a first end of a conduit fluidically coupled to the reservoir; delivering the coupled drainage device to a tissue pocket of an eye to dispose the collapsible body portion in an uncollapsed state with a planar configuration; retracting the delivery member from the drainage device to deploy the drainage device to be implanted at least in part within the tissue of the eye; and inserting a second end of the conduit into the eye to facilitate a drainage of the biological fluid into the conduit.

According to one example ("Example 65") further to Example 64, the planar configuration is defined by a curved plane corresponding to a curvature of the eye.

According to one example ("Example 66") further to Example 64 or 65, the collapsible body portion has a first length in an unfolded state in absence of an external force, a second length less than the first length in a folded state when the external force is applied, and a third length greater than the second length and less than the first length in a resting state after the external force is removed.

According to one example ("Example 67") further to Example 66, the third length is no greater than approximately 85% of the first length.

According to one example ("Example 68") further to any one of Examples 64-67, the method further includes attaching the drainage device to the tissue of the eye using at least one suture affixed to at least one suture hole on the collapsible body portion of the drainage device.

According to one example ("Example 69") further to any one of Examples 64-68, removably coupling at least the portion of the delivery member to the collapsible body portion of the drainage device includes: inserting a portion of the delivery member into the reservoir via the conduit to facilitate delivery of the drainage device to be implanted within the tissue of the eye. The delivery member is retracted from the reservoir after the drainage device is implanted.

According to one example ("Example 70") further to any one of Examples 64-69, the delivery member is a flexible delivery wire including a nickel-titanium alloy.

According to one example ("Example 71") further to any one of Examples 64-70, removably coupling at least the portion of the delivery member to the collapsible body portion of the drainage device includes: at least partially inserting the delivery member into a delivery member retaining portion formed on the collapsible body portion. The delivery member retaining position positioned outside of the reservoir and disconnected from the reservoir.

According to one example ("Example 72") further to Example 71, the delivery member retaining portion is a pocket formed at least partially in the collapsible body portion. The delivery member has a curved portion at a distal end which is at least partially receivable by the pocket.

According to one example ("Example 73") further to Example 71, the delivery member retaining portion is a delivery member conduit formed on an outer surface of the collapsible body portion. The delivery member is at least one flexible wire at least partially receivable within the delivery member conduit.

According to one example ("Example 74") further to Example 73, the delivery member conduit is positioned along a periphery of the reservoir or a periphery of the body member.

According to one example ("Example 75") further to Example 74, the delivery member conduit is positioned between the periphery of the reservoir and the periphery of the body member.

According to one example ("Example 76") further to any one of Examples 73-75, at least partially inserting the delivery member into the delivery member retaining portion includes: inserting a first flexible wire into the delivery member conduit via a first opening of the delivery member conduit and inserting a second flexible wire into the delivery member conduit via a second opening of the delivery member conduit such that the first flexible wire and the second flexible wire overlap within the delivery member conduit during delivery of the drainage device.

According to one example ("Example 77") further to any one of Examples 64-76, the collapsible body portion has a thickness of no greater than about 0.5 mm around the reservoir when the reservoir is empty.

According to one example ("Example 78"), a drainage device is configured to drain a biological fluid from an eye to a tissue external to the eye, the drainage device is implantable at least in part within a tissue of the eye, and the drainage device includes: a collapsible body portion defining a reservoir and a conduit having a first end fluidly coupled with the reservoir and a second end insertable into the eye to facilitate a drainage of the biological fluid into the conduit. The collapsible body portion, when collapsed, includes a deformation of the body portion from a first planar state to a second nonplanar state. In situ, the second nonplanar state is at least one of a folded state, a deformed state, a bent state, or a crumpled state.

The foregoing Examples are just that, and should not be read to limit or otherwise narrow the scope of any of the inventive concepts otherwise provided by the instant disclosure. While multiple examples are disclosed, still other embodiments will become apparent to those skilled in the art from the following detailed description, which shows and describes illustrative examples. Accordingly, the drawings and detailed description are to be regarded as illustrative in nature rather than restrictive in nature.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Definitions and Terminology

Figure 1A:
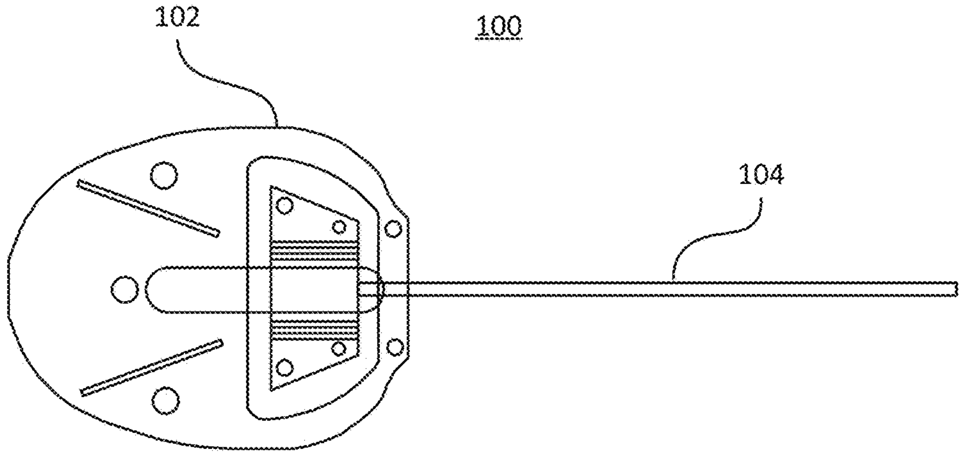
FIG. 1A (prior art)
FIG. 1A is a top view of a prior-art glaucoma drainage device.
Figure 1B:
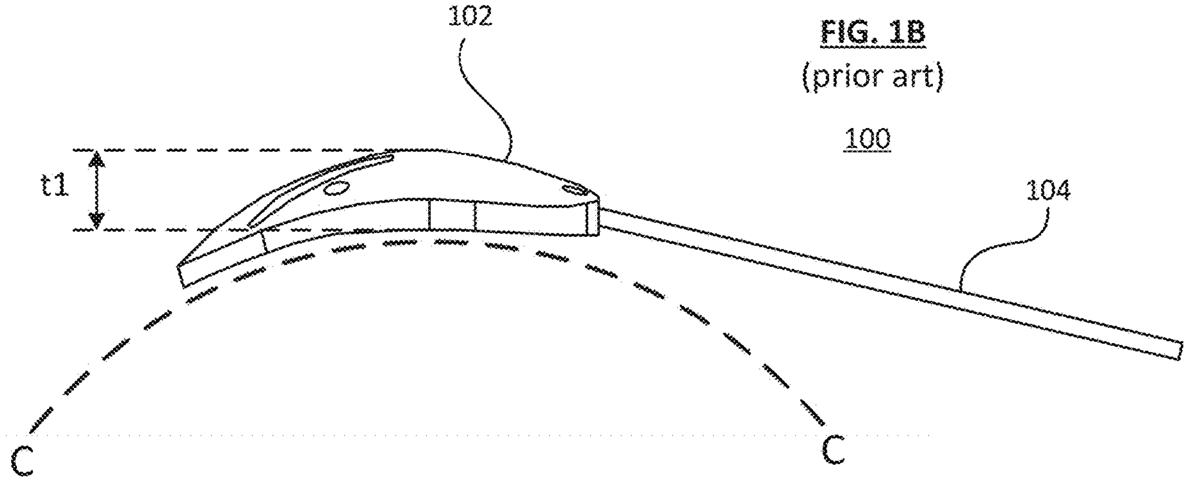
FIG. 1B (prior art)
FIG. 1B is a side view of the prior-art glaucoma drainage device of FIG. 1A.

This disclosure is not meant to be read in a restrictive manner. For example, the terminology used in the application should be read broadly in the context of the meaning those in the field would attribute such terminology.

With respect to terminology of inexactitude, the terms "about" and "approximately" may be used, interchangeably, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error, differences in measurement and/or manufacturing equipment calibration, human error in reading and/or setting measurements, minor adjustments made to optimize performance and/or structural parameters in view of differences in measurements associated with other components, particular implementation scenarios, imprecise adjustment and/or manipulation of objects by a person or machine, and/or the like, for example. In the event it is determined that individuals having ordinary skill in the relevant arts would not readily ascertain values for such reasonably small differences, the terms "about" and "approximately" may be understood to mean plus or minus 10% of the stated value.

Description of Various Embodiments

Persons skilled in the art will readily appreciate that various aspects of the present disclosure may be realized by any number of methods and apparatuses configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

As explained herein, there is a need for a thin flexible device that has a drainage and can be implanted into a tissue of the eye for treating glaucoma. Such device can readily comply with the surface contour of the eye without requiring preformed curvature in the structure of the device, so a single device can be compatible with the surface contour of any patient's eye, thereby eliminating the need to take measurements of the patient's eye prior to the implantation procedure and subsequently manufacture a device that is custom-fit for the patient's eye. Other benefits of using the thin flexible device will be recognized by those skilled in the art based on the disclosure.

Various features of devices, systems, and methods disclosed herein may be seen in FIGS. 2A-2D, 3A-3C, 4A-4B, 5A-5B, 6A-6B, and 7A-7C. Aspects of the present disclosure relate to drainage devices, systems, and methods for biological fluids. More particularly, the present disclosure relates to devices, systems, and methods for draining aqueous humor from the anterior chamber 'AC' of an eye 10 of a patient so that the aqueous humor may be resorbed by the body elsewhere.

Figure 2A:
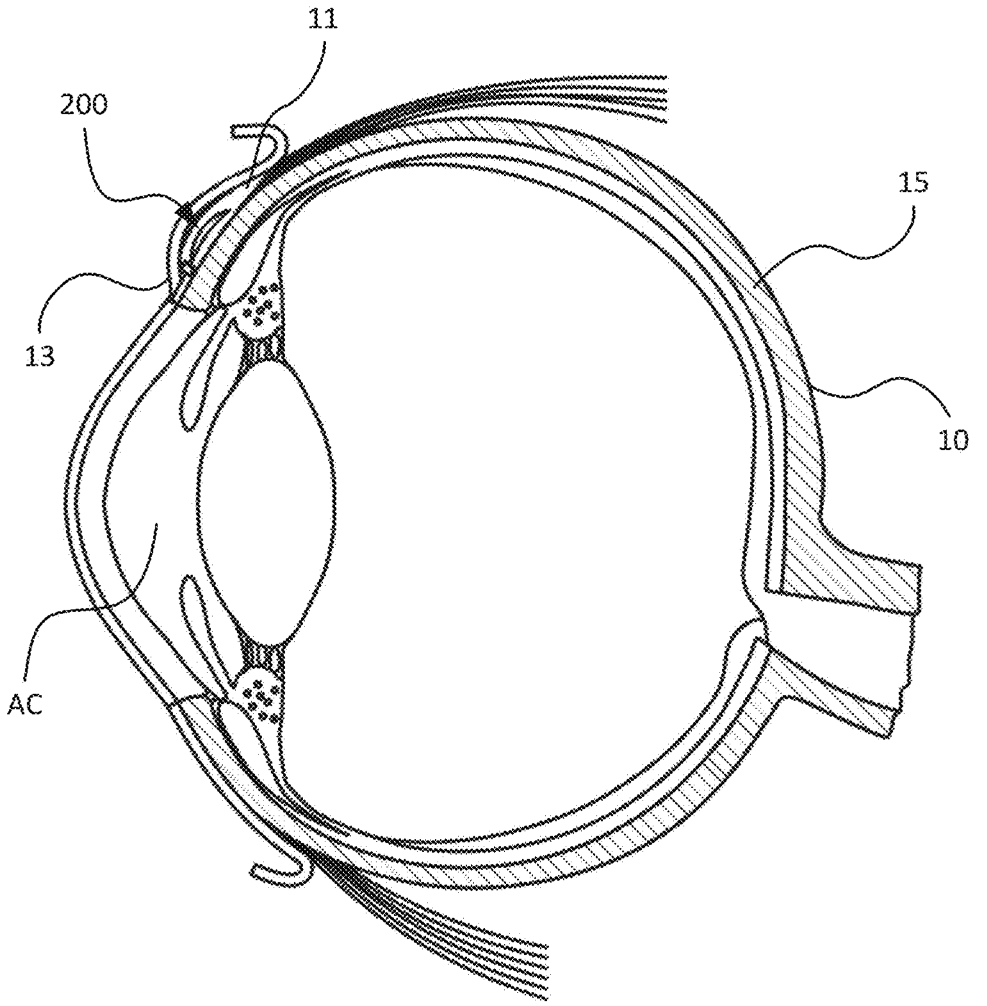
FIG. 2A is a cross-sectional side view of an eye with a drainage device implanted therein consistent with various aspects of the present disclosure.

To that end, FIG. 2A is an illustration of an eye 10 with a subconjunctival space 11 between a conjunctiva 13 and a sclera 15 of the eye 10. Implanted within the eye 10 is a drainage system with a drainage device 200 in accordance with principles of the present disclosure. In an aspect of the present disclosure, a mechanism is provided for reabsorption of aqueous humor that has been expelled from the anterior chamber 'AC' of the eye 10 to reduce or otherwise stabilize intraocular pressure. One skilled in the art, however, will appreciate that aspects of the present disclosure are useful in other applications where drainage of biological fluid to be redirected in the body is desired.

Figure 2B:
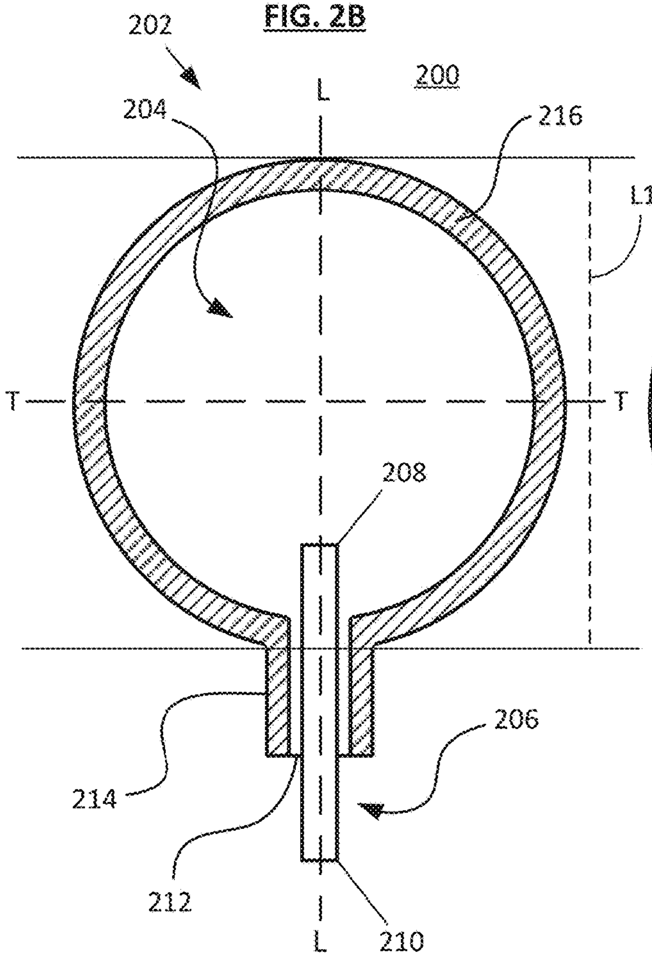
FIG. 2B is a cross-sectional top view of the drainage device from FIG. 2A according to some embodiments disclosed herein.
Figure 2C:
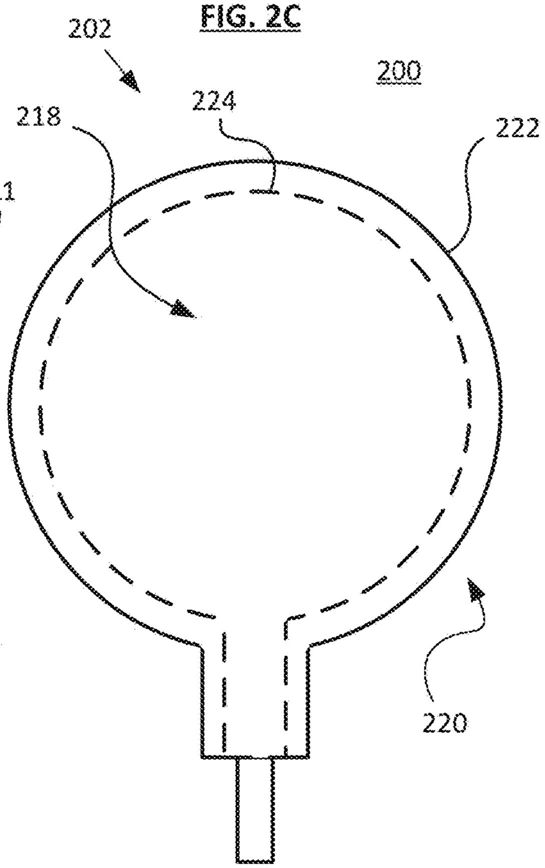
FIG. 2C is a top view of the drainage device from FIG. 2A according to some embodiments disclosed herein.
Figure 2D:
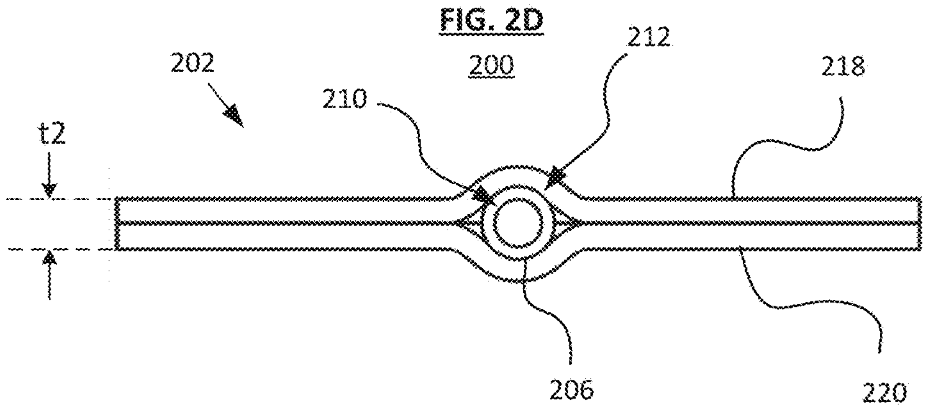
FIG. 2D is a side view of the drainage device from FIG. 2A according to some embodiments disclosed herein.

FIGS. 2B-2D illustrate the drainage device 200 for treating glaucoma according to some embodiments. As illustrated here, the glaucoma drainage device 200 has a body portion 202 that has a first side 218 and a second side 220, according to some examples. The second side 220 may be the side that is facing the eye, and the first side 218 faces away from the eye, when the drainage device 200 is implanted. The body portion 202 in some examples assumes a planar configuration (also referred to as a "first planar state") and is also collapsible in a manner that is foldable, deformable, bendable, or crumplable, i.e., capable of being crumpled (where the collapsed configuration may be referred to as a "second nonplanar state"). It is to be understood that the word "planar" may refer to a Euclidean plane or to a plane according to a different geometry such as a generally spherical geometry, where a plane would refer to a two-dimensional surface of a sphere resembling an eye. As such, a planar configuration of the drainage device may assume a flat shape or assume a shape having a contour or curvature, for example one that is generally consistent with the contour or curvature of a surface of the eye.

In some examples, the first side 218 and the second side 220 each comprises a separately formed layer that is attached or adhere to each other to form the body portion 202. Although discussed below in connection with an intake conduit 206, it should be understood that the drainage device 200 may be a standalone product so long as some portion thereof is configured to receive fluid (e.g., directly from an incision, from the conduit 206, etc.) and as such should not be considered outside the scope of this disclosure. Fluidly coupled to the drainage device 200 may be an intake conduit 206. When implanted, the intake conduit 206 extends from the anterior chamber 'AC' of the eye 10 to the drainage device 200. The aqueous humor at the anterior chamber 'AC' then flows through intake conduit 206 and into the drainage device 200.

In some examples, only the second side 220 may be present in the body portion 202 such that the intake conduit 206 is positioned on a surface of the second side 220 that is facing away from the eye. In some examples, the presence of the second side 220 alone is sufficient to keep a bleb located under the exterior surface tissue of the eye 10 (i.e., the conjunctiva 13) which is formed during the procedure from healing or closing. In some examples, the second side 220 can be thin and flexible such that the second side 220 is collapsible (e.g., foldable, deformable, bendable, or crumplable) or otherwise having the structural features described herein for the body portion 202.

Material selection of the drainage device 200 may contribute to its functionality and relatively low profile in comparison to other devices known in the art. The drainage device 200 may comprise biocompatible materials, including microporous materials such as expanded polytetrafluoroethylene (ePTFE) as discussed below. The intake conduit 206 may include biocompatible materials that are flexible and suitable for use in constructing elongate members. Some such suitable materials may include silicone, polytetrafluoroethylene, polypropylene, polymethyl methacrylate, acrylic, polyurethane, silastic, and metal. Such construction of the drainage device 200 is particularly useful for surgical implantation. In some examples, the drainage device 200 has a maximum thickness "t2" of less than approximately 1 mm, less than approximately 0.8 mm, less than approximately 0.5 mm, less than approximately 0.3 mm, less than approximately 0.1 mm (100 microns), less than approximately 80 microns, less than approximately 50 microns, less than approximately 30 microns, less than approximately 10 microns, or any other suitable value or range therebetween. The maximum thickness is measured when the reservoir is empty and uninflated.

In general, surgical implantation of drainage devices, such as the drainage device 200, involve risk of abnormal pressures within the eye 10. For instance, when drainage devices are surgically implanted, such as in surgeries that require the creation of a bleb under the exterior surface tissue of the eye 10 (i.e., the conjunctiva 13), surrounding tissues fresh from the insult of the surgery do not provide appreciable flow resistance to aqueous flow until sufficient wound healing occurs. During this early post-operation period, the patient is at risk of hypotony of the eye 10 (e.g., too low eye pressure). To avoid hypotony, measures are taken to manage flow through the drainage device 200 for a period of time. For example, surgeons traditionally lie-off a portion of the intake conduit 206 near its proximal end for a period of time and release the tie after surgical wound healing has sufficiently progressed such that the surrounding tissue will provide the necessary flow resistance. In certain commercial glaucoma shunt devices, a restrictive flow 'valve' is added distal of the intake conduit 206 where a plate section is located. These devices, however, are relatively stiff and bulky and still may result in hypotony. To the contrary, advantageously, drainage devices, systems, and methods according to principles of the present disclosure include low profile devices that generate appreciable flow resistance in the early post-operation period, e.g., to avoid hypotony.

In this example, the drainage device 200 is disposed in a subconjunctival space 11 between the conjunctiva 13 and the sclera 15 of the eye 10. The drainage system 200 may be oriented such that the first layer 218 extends along the sclera 15 and such that the second layer 220 extends along the conjunctiva 13. It will be appreciated that the portion of the second layer 220 that interfaces with the conjunctiva 13 may be configured to promote or permit tissue ingrowth, as discussed below. It will also be appreciated that the portion of the first layer 218 that interfaces with the sclera 15 may additionally or alternatively be configured to promote or permit tissue ingrowth, as discussed below. Such configurations help minimize relative movement between the drainage device 200 and the surrounding tissue.

In configurations with a drainage device having only a single layer (that is, only the second side 220 without the first side 218), the device may be disposed such that a first surface of the single layer is positioned facing the eye, while a second surface of the single layer is positioned away from the eye. In some examples, the reservoir of the drainage device remains open, and any fluid flowing into the intake conduit 206 may be allowed to flow out into an environment surrounding the drainage device, without being contained within the drainage device.

Moreover, the intake conduit 206 is shown as extending from the drainage device 200, and extending through a scleral access, perforation, or hole 'H' (e.g., made by a physician during the implantation procedure according to known methods) such that a first end 208 (e.g., a distal end) is fluidly coupled with a reservoir 204 inside the body portion 202 (and at least partially defined by the body portion 202) and a second end 210 (e.g., a proximal end) accesses the anterior chamber 'AC' and places a port in communication therewith. In some embodiments, when implanted, aqueous humor enters the second end 210 of the intake conduit 206 and travels to the first end 208 of the intake conduit 206 in fluid communication with the drainage device 200. Together, the body portion 202 and the intake conduit 206 may define a flow passage along which the drainage flows through the drainage device 200. In some embodiments, the first end 208 is positioned within the drainage device 200 such that the evacuated aqueous humor enters the reservoir 204 defined within the drainage device 200 and penetrates through the various diffusion membranes of the drainage device 200, where the aqueous humor is then absorbable by the surrounding and/or ingrown tissue.

In some examples, the intake conduit 206 is positioned along a longitudinal axis L-L of the drainage device 200 which extends through the center of the drainage device 200, for example. In some examples, the body portion 202 of the drainage device 200 includes a flap 214 which is continuously formed from the same material comprising the body portion 202 such that the flap 214 and the body portion 202 define a unitary component. The flap 214 defines an opening 212 in which the conduit 206 may be inserted, and the portion of the flap 214 surrounding the conduit 206 may be adhered together to prevent the fluid within the reservoir 204 from leaking out through the opening 212. In some examples, as shown in FIG. 2D which is viewed along the longitudinal axis L-L, the opening 212 surrounding the conduit 206 may be left partially open to provide excess fluid within the reservoir 204 to escape, as suitable. The flap 214 may function as a patch graft or coverage component which covers the exposed portion of the conduit 206 which remains external to the eye tissue, after which the flap 214 may be sutured into place and the conjunctiva 13 is closed, after the drainage device 200 is implanted. The body portion 202 has a first length "L1," also referred to as its full length, when laid out on a flat surface. The length L1 may be measured from a first end, such as the end of the body portion 202 where the flap 214 beings, or where the conduit 206 reaches the reservoir 204, to an opposing second end, such as the top of the body portion 202 that is farthest from the first end. The measurement may be taken along or parallel to the longitudinal axis. Also shown is a transverse axis T-T that is transverse to the longitudinal axis L-L. By definition, the transverse axis is not parallel to the longitudinal axis. The transverse axis may intersect the longitudinal axis at any suitable angle, for example an acute angle, perpendicular angle, or obtuse angle.

In some examples, adhesive 216 is applied on the first layer 218 or the second layer 220 between a periphery 222 of the body portion 202 and a periphery 224 of the reservoir 204. The first and second layers 218 and 220 are attached together to form the body portion 202.

Figure 3A:
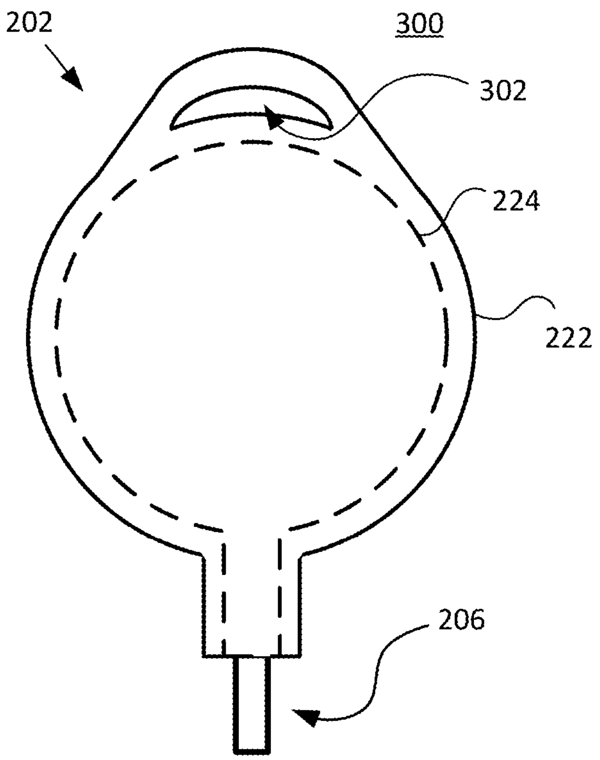
FIG. 3A is a top view of a drainage device according to some embodiments disclosed herein.
Figure 3B:
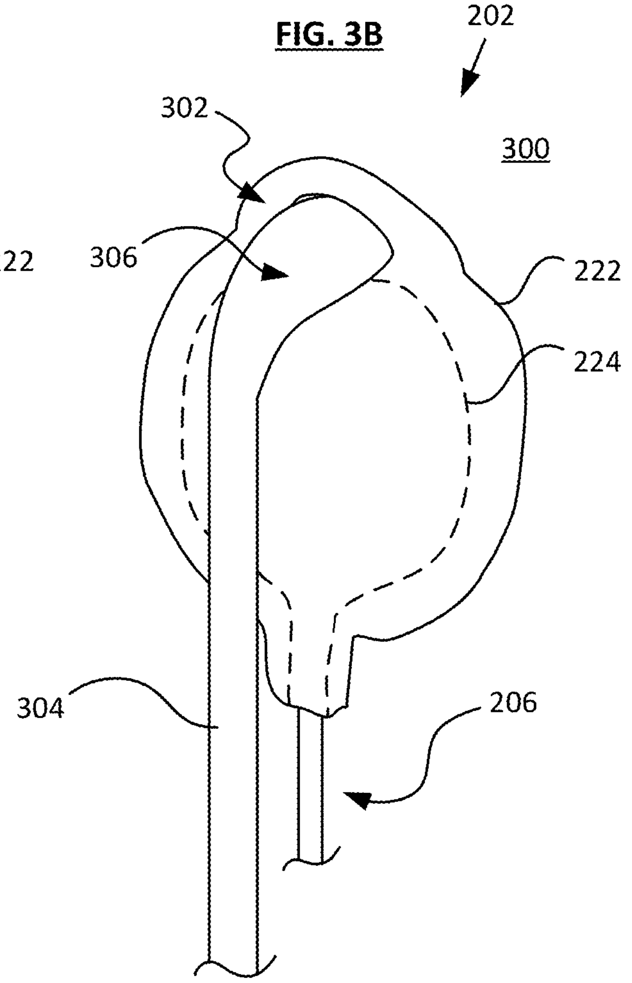
FIG. 3B is an angled view of the drainage device of FIG. 3A with a delivery member engaged therewith, according to some embodiments disclosed herein.
Figure 3C:
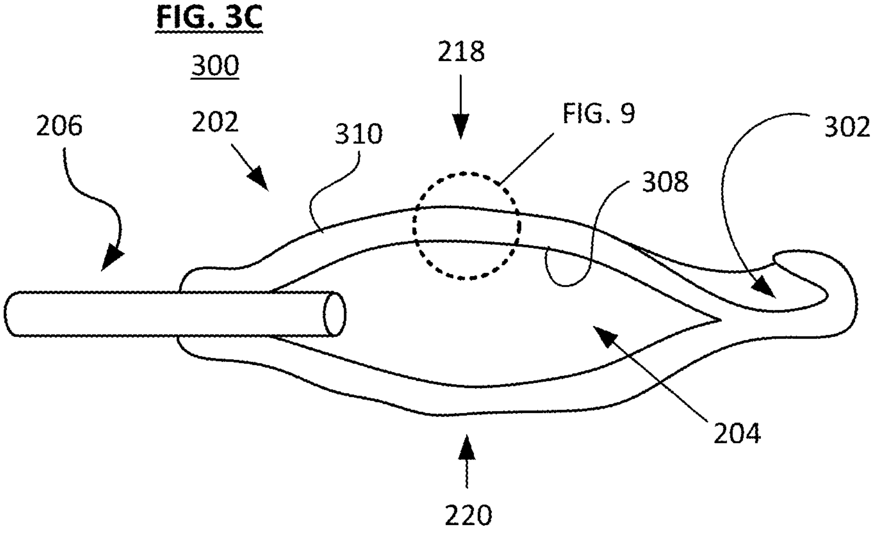
FIG. 3C is a cross-sectional side view of the drainage device of FIG. 3A, according to some embodiments disclosed herein.

FIGS. 3A through 3C illustrate another example of a drainage device 300 according to some embodiments disclosed herein. The drainage device 300 includes the body portion 202 and the conduit 206, and the body portion 202 further includes a delivery member retaining portion 302 formed in the body portion between the periphery 222 and the periphery 224. The retaining portion 302 is any suitable feature that retains at least a portion of a delivery member in order to facilitate delivery of the drainage device 300 to a target location of the body, such as the treatment side of the eye. The retaining portion 302 may be a cavity, compartment, pocket, pouch, receptacle, or sack, for example, which is formed in the body portion 202 to at least partially receive at least a portion of any suitable delivery member, such as a delivery member 304 shown in FIG. 3B. Specifically, the delivery member 304 may resemble a spoon-like shape, that is, the delivery member 304 may have a straight portion and a curved portion 306 at or near its distal tip which is at least partially inserted into the retaining portion 302 so that as the delivery member 304 is pushed in one direction, the drainage device 300 is also advanced in the same direction but in a pulling motion (via a pulling force) following the delivery member 304, thereby facilitating delivery of the drainage device 300 to the target location without having the drainage device experience excessive collapsing of the device, such as over-flexing, folding, deforming, bending, or crumpling of the body portion, for example. As such, the retaining portion 302 may be suitably sized and positioned to convey the pulling force to the body portion 202 to maintain the body portion in the planar state during implantation. The pulling force may be supplied by the delivery member 304 upon engaging with the retaining portion. In some examples, the delivery member 304 may be a Descemet membrane endothelial keratoplasty (DMEK) spoon, a double-ended orbital globe retractor-elevator as sold by Rumex®, or any other suitably sized surgical spatula as known in the art.

FIG. 3C shows how the retaining portion 302 is located separately from the reservoir 204 such that the retaining portion 302 does not have fluid connection with an inner surface 308 of the body portion 202, but rather may be an extension of an outer surface 310 of the body portion 202. The inner surface 308 and the outer surface 310 may refer to the surfaces of either of the first body layer 218 or the second body layer 220 forming the body portion 202. In some examples, there may be more than one such retaining portion, such as a plurality of retaining portions, each capable of receiving at least a portion of any suitable delivery member. In some examples, different retaining portions may be configured to accommodate receiving therein different types of delivery member.

Figure 4A:
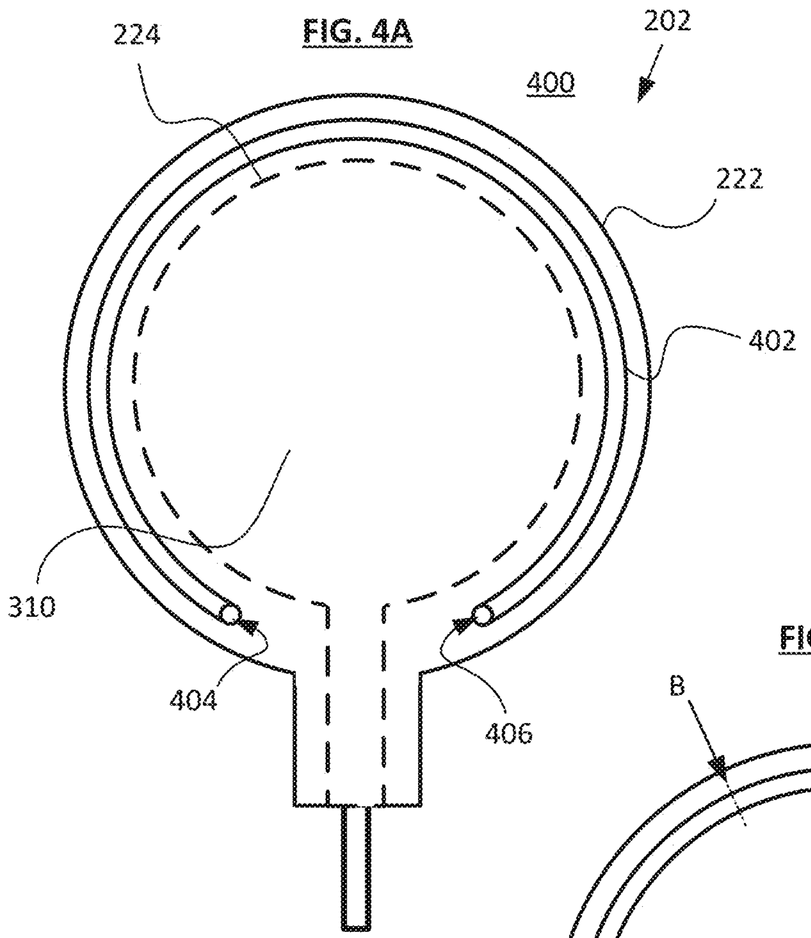
FIG. 4A is a top view of a drainage device according to some embodiments disclosed herein.
Figure 4B:
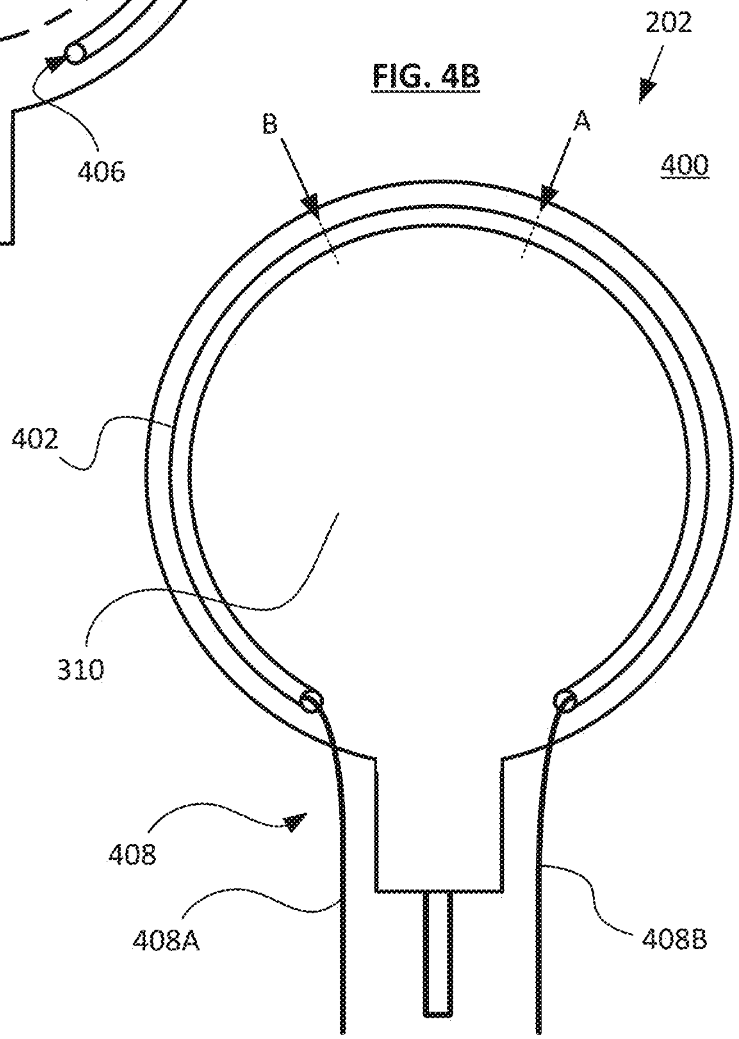
FIG. 4B is a top view of the drainage device of FIG. 4A with one or more delivery member extending through its delivery member conduit, according to some embodiments disclosed herein.

FIGS. 4A and 4B illustrate another example of a drainage device 400 according to some embodiments disclosed herein. The drainage device 400 includes a delivery member conduit 402 positioned on an external or outer surface 310 of the body portion 202 of the drainage device 400. The conduit 402 may be formed of any suitable material and have any suitable shape, such as tubular or other hollow structure, as long as the configuration allows a removable engagement with a stiffening element or support member used during the implantation procedure. The conduit 402 may be formed separately from the body portion 202 and then subsequently attached or adhered to the outer surface of the body portion 202 when forming the drainage device 400. The conduit 402 may be positioned between the peripheries 222 and 224. The conduit 402 has two openings: a first opening 404 and a second opening 406, which may define the two ends of the conduit 402. In some examples, the openings may be located on an intermediate portion of the conduit 402 that is between the two ends. In some examples, there may be more than two openings in the conduit 402, for example when the conduit is formed from a series of "belt loops," or a plurality of separately formed conduits of shorter lengths lined up along the periphery of the body portion 202 rather than a single continuous conduit.

In an embodiment, one or more support members 408 may be temporarily inserted into the conduit 402 through the first opening 404 and/or the second opening 406 in order to provide structural stability to the drainage device 400 during delivery, that is, to prevent the drainage device 400 from wrinkling or folding or bending onto itself during delivery. The support member(s) 408 may be made using any suitable material which allows for sufficient rigidity to maintain the structure of the drainage device 400 during delivery but also allows for sufficient flexibility such that the support member(s) 408 may be inserted into the delivery member conduit 402 and conform to its internal structure (and curvature, for example) without tearing the wall of the conduit 402 or deforming the conduit 402 and/or the drainage device 400. In some examples, the support member(s) 408 may be one or more wires. In another example, the conduit 402 may provide a passage for a stiffening element (the support member) that temporarily increases the stiffness of the device 400 such as, for example, a coiled wire that assumes a stiff configuration when axially twisted and a relaxed configuration when untwisted. In another example, the conduit 402 may be pressurized to increase the stiffness of the device 400 along a length of the pressurized conduit 402. The pressure may be released once the device 400 is in a target position and the stiffness of the device 400 can be reduced or removed such that the device 400 is allowed to assume a fully relaxed state.

FIG. 4B shows an example in which two wires 408 are inserted into the conduit 402 to provide support for the drainage device 400 during delivery. Each of the wires 408 has an axial strength or stiffness that allows the wires to be pushed or advanced distally without significant flexing in order to advance the supported drainage device 400. For example, a first wire 408A may be inserted into the first opening 404, and a second wire 408B may be inserted in to the second opening 406. Inside the conduit 402, a portion of each wire may overlap with a portion of the other wire. For example, the distal tip of the first wire 408A may extend until point "A," and the distal tip of the second wire 408B may extend until point "B," such that there is an overlap of the two wires between points "A" and "B." The overlap may be beneficial in providing increased support for the distal portion of the drainage device 400 (that is, the portion proximal to the overlapped portion of the wires between points "A" and "B") when the user pushes the drainage device 400 forward (distally) when delivering the body portion of the drainage device into the tissue for implantation. Once delivered, the wires 408A and 408B may be pulled or retracted (proximally) to release the drainage device 400 therefrom. The support member, stiffening element, or wire as explained herein can also be referred to as a "temporary reinforcement element" which reinforces or maintains the collapsible body portion in the planar state. In some examples, the body portion 202 may include both the retaining portion 302 (which may be a cavity, compartment, pocket, pouch, receptacle, or sack, for example) of FIGS. 3A-C and the delivery member conduit 402 for receiving the wire(s) 408 of FIGS. 4A-B, as suitable, such that the delivery of the drainage device may be facilitated using any one or more means or methods of delivery as explained above.

Figure 5A:
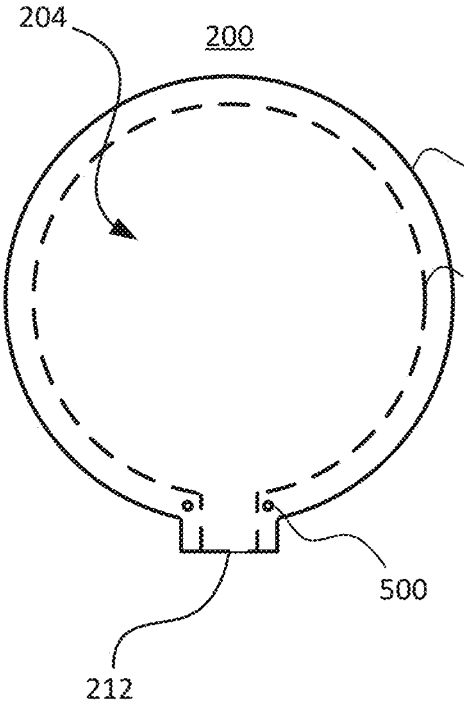
FIG. 5A is a top view of a drainage device according to some embodiments disclosed herein.

FIG. 5A shows an example of the drainage device 200 where one or more holes 500 is formed on the body portion 202 between the peripheries 222 and 224. The holes 500 may be positioned proximal to the opening 212 of the body portion 202 such that the holes 500 can be utilized as visual indicators showing the position and location of the opening 212 of the body portion 202 when implanting the drainage device 200. In some examples, one or more sutures may pass through the holes 500 to immobilize the implanted drainage device 200 at the target location. The placement of the holes 500 is preferably at the proximal end of body portion 202 near the opening 212, such that the device can be anchored to a tissue with sutures at the proximal end of the body portion 202 while the distal end of the body portion 202 remains free to move relative to the anchoring before, during, and/or after the reservoir 204 of the body portion 202 inflates and deflates, in some examples.

Figure 5B:
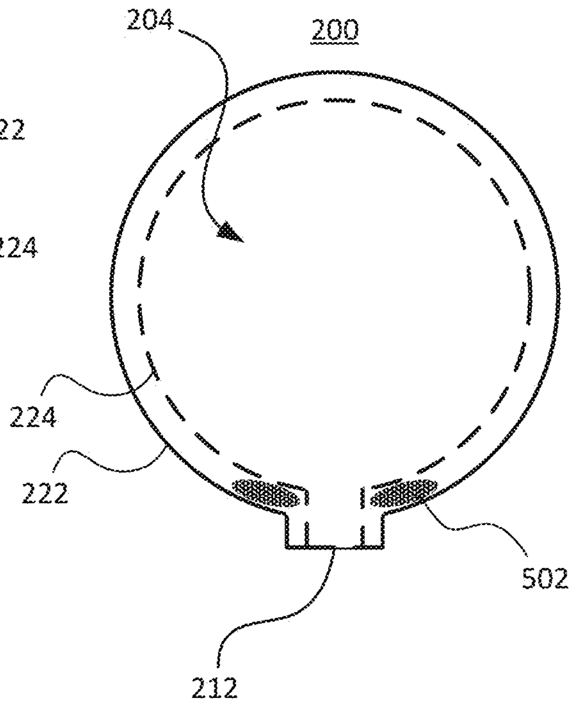
FIG. 5B is a top view of a drainage device according to some embodiments disclosed herein.

FIG. 5B shows an example of the drainage device 200 where one or more markers 502 are used to locate the opening 212, instead of the holes 500. In some examples, the markers 502 may be radiopaque markers or colored markings located on the outer surface 310 of the drainage device 200 or between the layers 218 and 220 forming the body portion 202 of the drainage device 200.

Figure 6A:
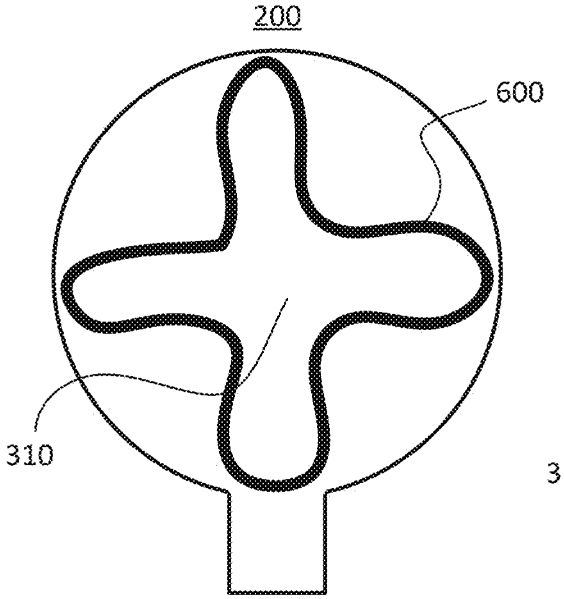
FIG. 6A is a top view of a drainage device according to some embodiments disclosed herein.
Figure 6B:
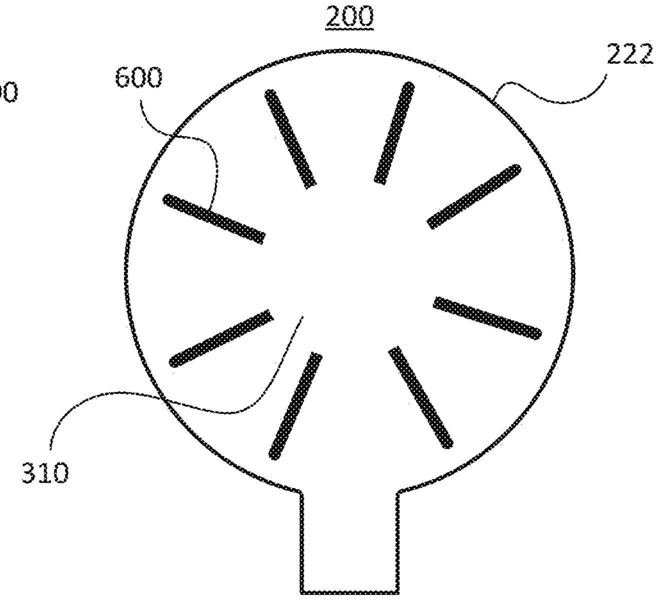
FIG. 6B is a top view of a drainage device according to some embodiments disclosed herein.

FIGS. 6A and 6B show examples of the drainage device 200 with adsorbable support members 600 located on the outer surface 310 of the body portion 202 which provide structural support for the drainage device 200 during delivery. For example, there may be a single support member (as in FIG. 6A) or multiple support members (as in FIG. 6B) having a shape or configuration suitable to reduce wrinkling or collapsing, for example folding, deforming, bending, or crumpling, of the drainage device 200 during delivery. The support member may have any suitable configuration such as a cross-shaped configuration of FIG. 6A or straight members extending radially from the center of the body portion 202 toward the periphery 222 of the body portion 202 as shown in FIG. 6B. In some examples, the adsorbable support members 600 may adsorb partially or completely into the surrounding environment after a period of time. As such, the adsorbable support member as explained herein can also be referred to as a "temporary reinforcement element." In some embodiments, the adsorbable support members 600 may be placed within the reservoir 204 defined by the body portion 202 to provide support to the drainage device 200 during implantation. As can be appreciated, body fluids entering the reservoir after implantation can dissolve the support members 600.

Figure 7A:
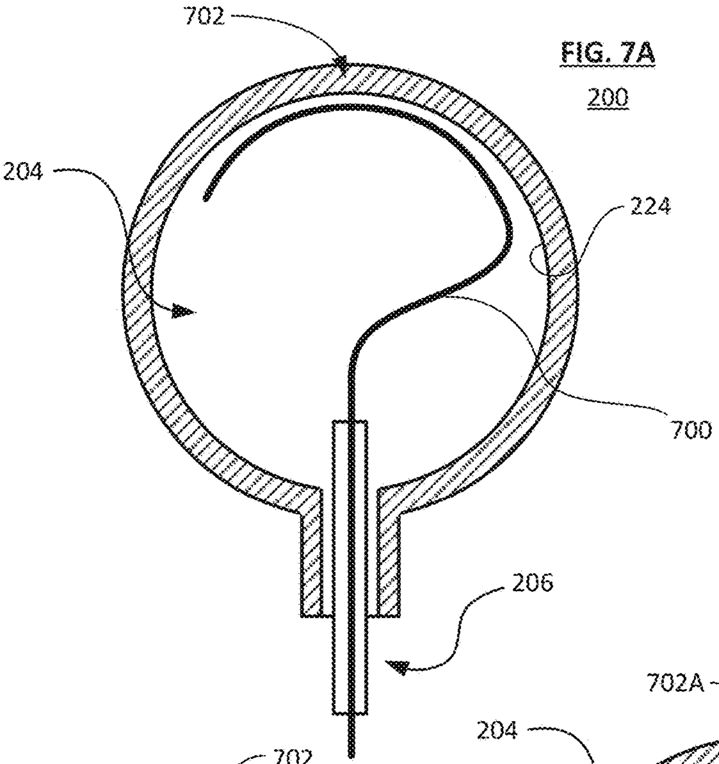
FIG. 7A is a cross-sectional top view of the drainage device with a delivery member according to some embodiments disclosed herein.
Figure 7B:
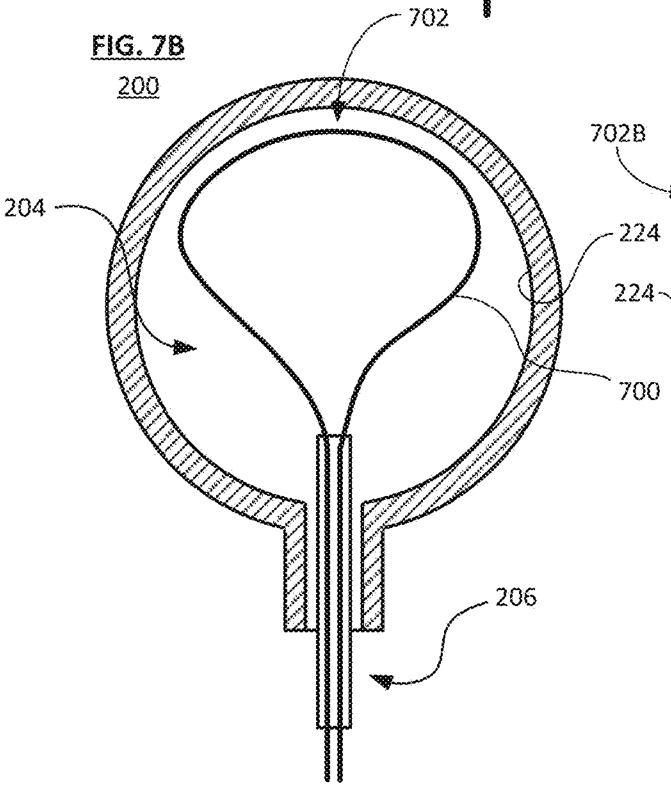
FIG. 7B is a cross-sectional top view of the drainage device with another delivery member according to some embodiments disclosed herein.
Figure 7C:
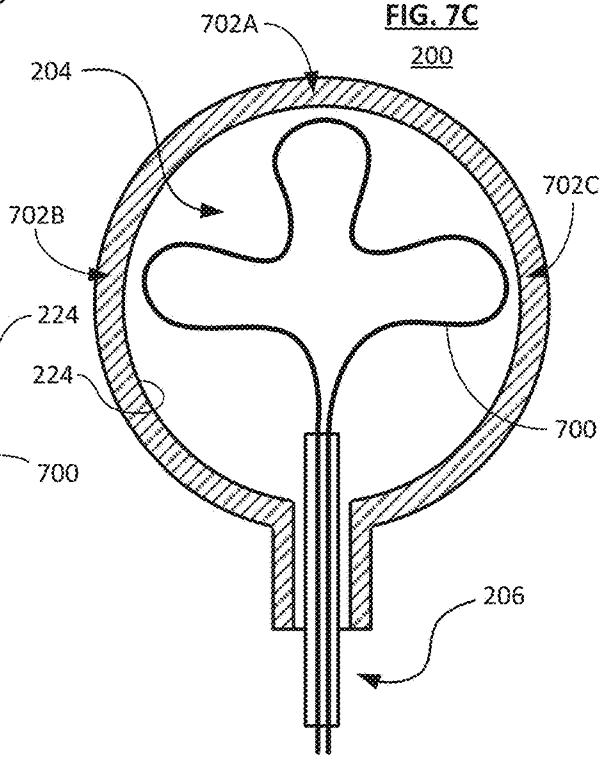
FIG. 7C is a cross-sectional top view of the drainage device with yet another delivery member according to some embodiments disclosed herein.

FIGS. 7A through 7C show examples of the drainage device 200 where the support member is provided internal to the reservoir 204 during delivery. For example, in FIG. 7A, a support member 700, which may be a suitably flexible wire, may extend into the reservoir 204 of the drainage device 200 and forms a curved portion 702 (similar to a question mark) such that the curved portion contacts the periphery 224 of the reservoir 204 inside the drainage device 200, after which the user may deliver the drainage device 200 to the target location without causing the drainage device 200 to be wrinkled or collapsed (e.g., folded, deformed, bent, or crumpled) during delivery.

In FIG. 7B, both ends of the support member 700 are located outside the drainage device 200 but a curved intermediate portion 702 of the support member 700 is curved along the periphery 224 of the reservoir 204 to facilitate support for the drainage device 200 during delivery. In FIG. 7C, the support member 700 forms a plurality of curved intermediate portions 702A, 702B, and 702C as shown, where a portion of each curved portion is configured to contact the periphery 224 of the reservoir 204 to prevent the drainage device 200 from wrinkling or collapsing (e.g., folding, deforming, bending, or crumpling) during delivery. In the above examples, the support member 700 may enter and exit the reservoir 204 via the intake conduit 206, allowing the support member to be withdrawn from the drainage device 200 after delivery, for example, by pulling on one end of the support member, or in some cases both ends of the support member. Therefore, the support member as explained herein can also be referred to as a "temporary reinforcement element." As can be appreciated in the embodiments illustrated in FIGS. 7A-7C, the support member 700 can extend solely in a flat plane aligned with the cross-sectional view of the drainage device 200. Alternatively, the support member 700 can extend in multiple directions both towards the eye and away from the eye to provide non-axial support to the device as the device is inserted into position in an axial direction. Alternatively, the support member 700 can extend along a curved plane defined by the curvature of the eye, for example as defined by the spherical geometry of the eye.

Figure 8A:
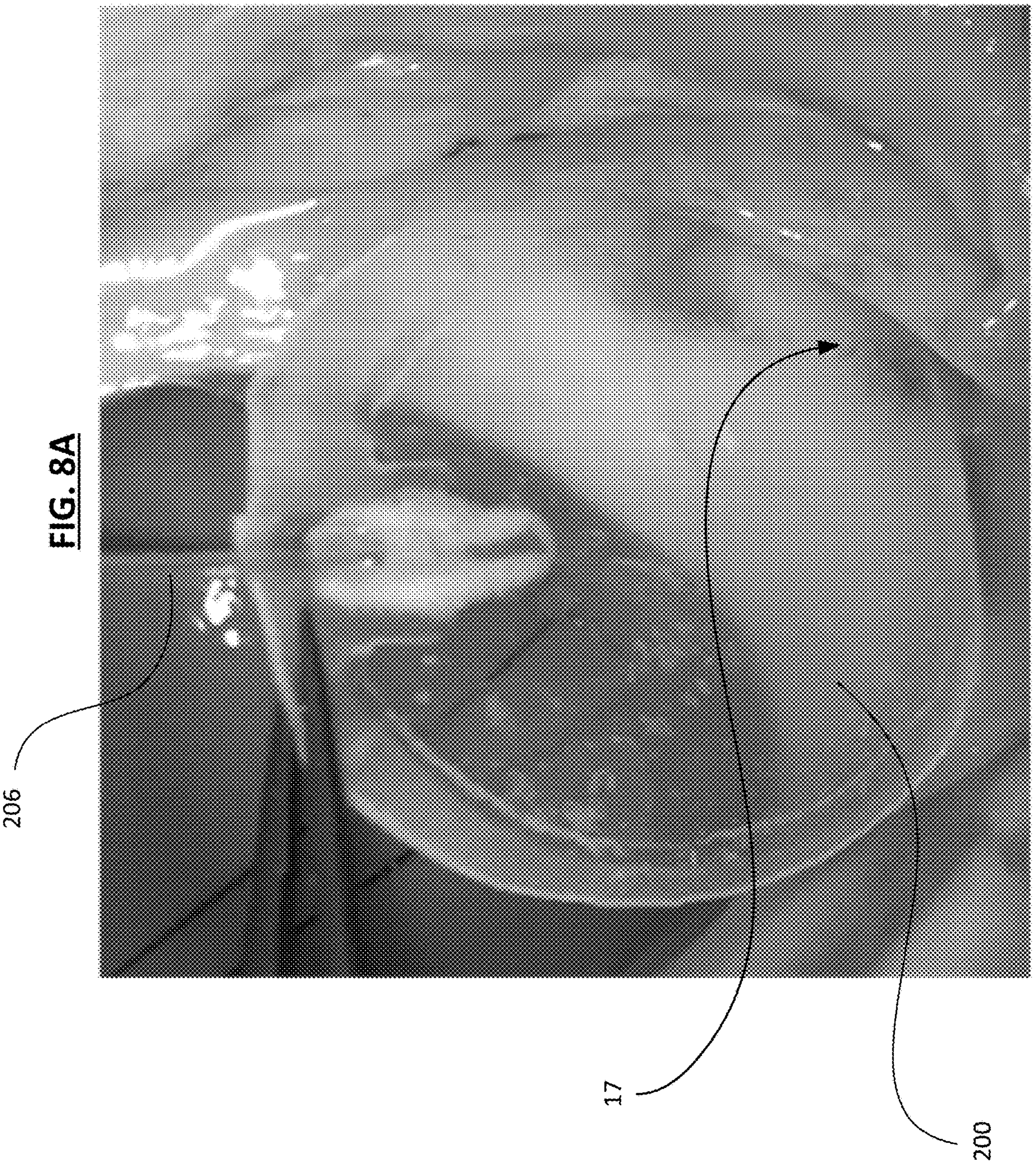
FIGS. 8A through 8D are images of the drainage device being implanted in the eye tissue in different configurations according to some embodiments disclosed herein.

FIGS. 8A through 8D show different methods of implanting an exemplary embodiment of the drainage device 200 described in the other embodiments as disclosed herein. In FIG. 8A, the drainage device 200 is laid flat and inserted into the cut or incision 17 into the tissue of the eye by holding the proximal end (or anterior rim, near the intake conduit 206) using any suitable tool such as non-toothed forceps and advancing the drainage device 200 into the subconjunctival space formed by the incision 17 while the pocket is held open. To prevent the device 200 from folding or bending onto itself, the support member(s) as disclosed herein may be implemented.

Figure 8B:
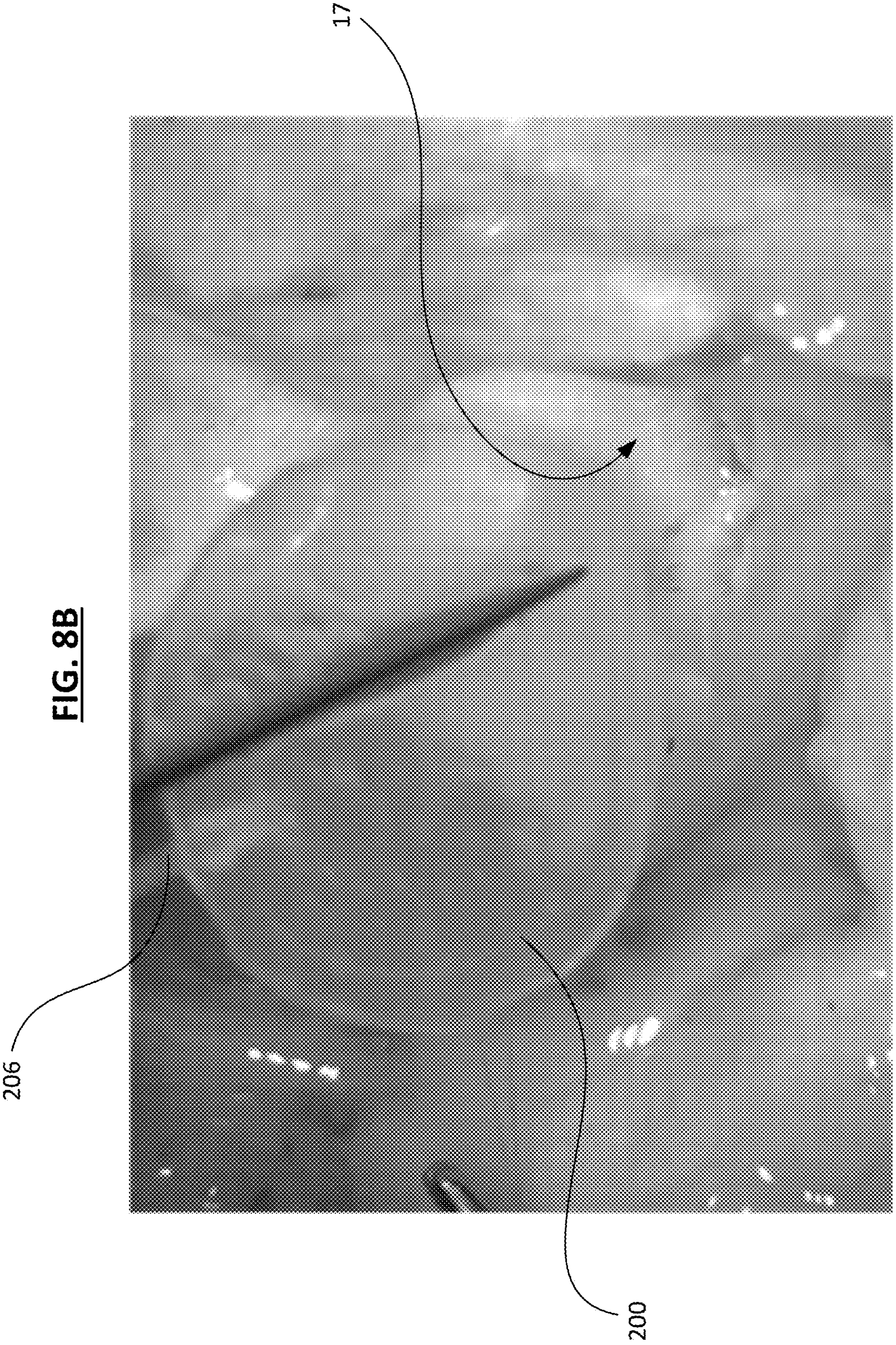

In FIG. 8B, the drainage device 200 is held using the forceps such that the distal end (or posterior rim) of the device 200 is grasped to be substantially parallel with the conduit 206. This method facilitates delivery of the device 200 at the desired depth with little undesired longitudinal folding or bending, that is, folding or bending along the longitudinal axis defined by the forceps (e.g., along the axial length L-L shown in FIG. 2B). In some examples, the drainage device 200 may experience folding or bending along the transverse axis T-T (also shown in FIG. 2B) during the procedure, but such folding or bending is less detrimental than the longitudinal folding or bending and can be corrected by "smoothening" such folds or bends using the forceps or another tool after delivery, for example.

Figure 8C:
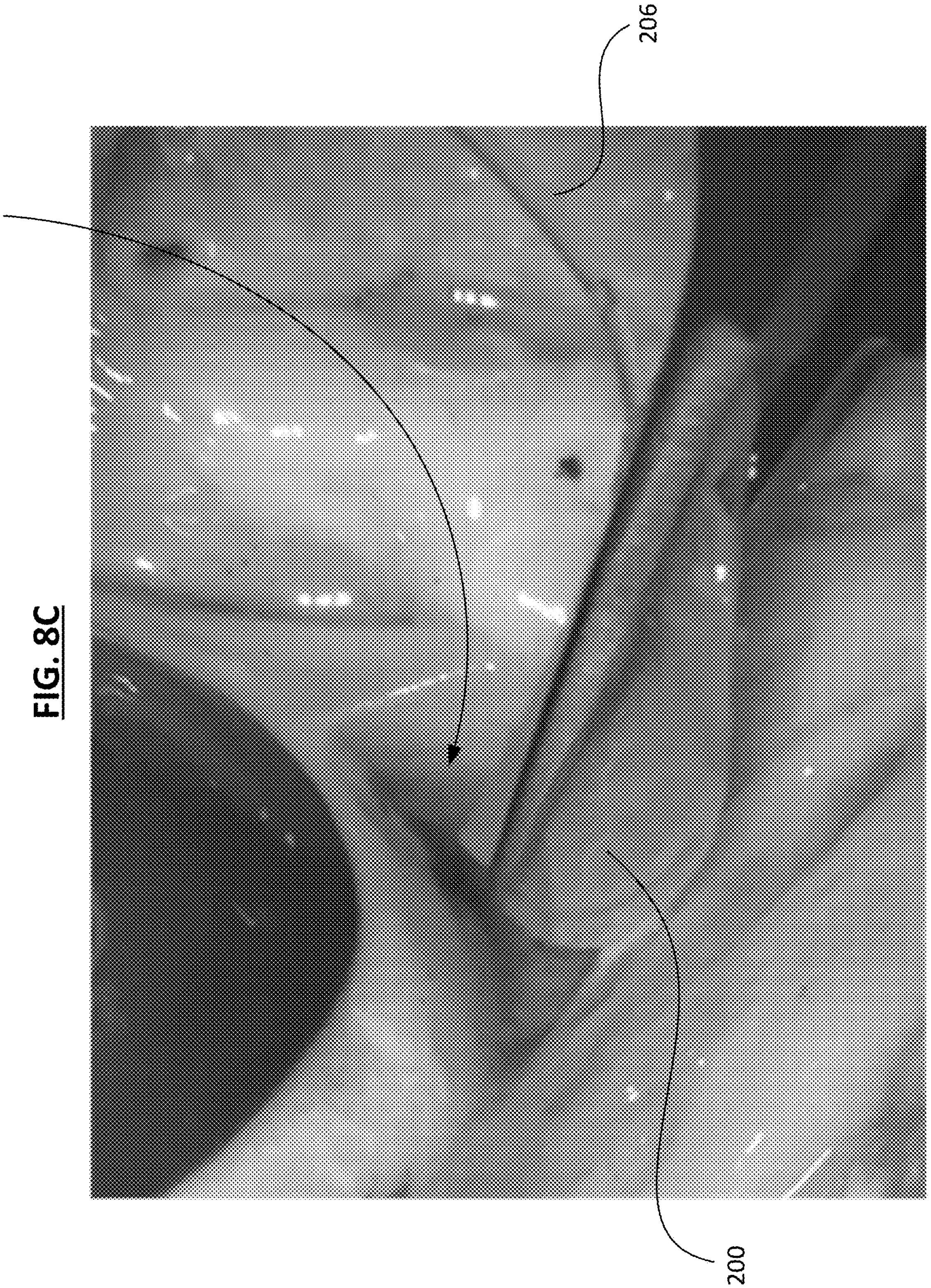

In FIG. 8C, the drainage device 200 is folded or bent axially (that is, the fold or bend takes place either at the longitudinal axis L-L or along a line parallel to the axis) and the distal end or posterior rim of the device 200 is grasped using the forceps such that the forceps are substantially parallel with the conduit 206. The device 200 is pushed forward into the subconjunctival space inside the pocket formed by the incision 17. This method also facilitates delivery of the device 200 at the desired depth with little undesired axial folding or bending.

Figure 8D:
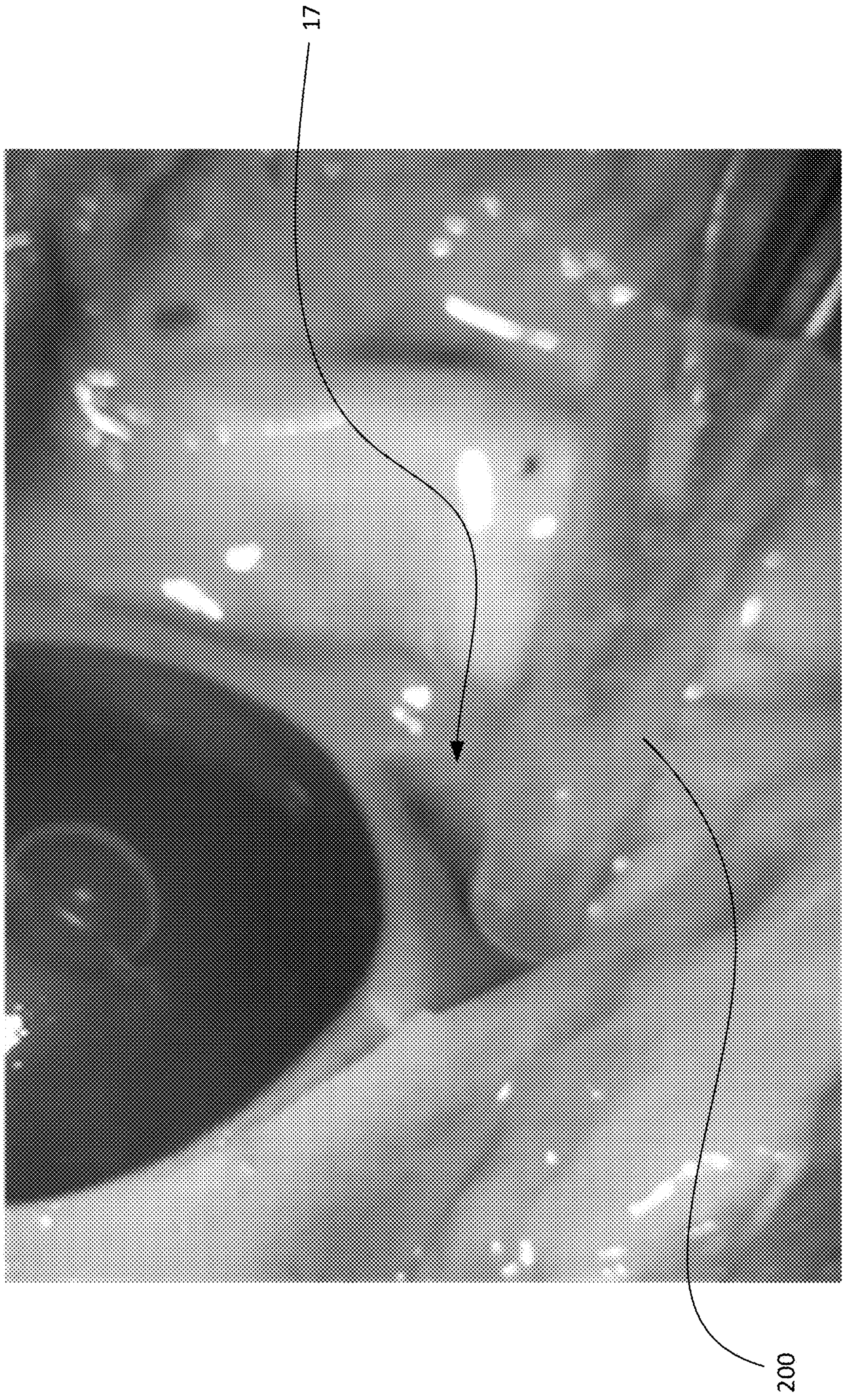

In FIG. 8D, the drainage device 200 is grasped on one lateral edge with the forceps approximately parallel with the conduit 206. The device 200 is then rolled or wrapped around the body of the forceps and subsequently pushed into the subconjunctival space. After the device 200 is inserted, it is unrolled or unwrapped in situ within the subconjunctival space. This method also facilitates delivery of the device 200 at the desired depth with sufficient axial stiffness and little undesired axial folding or bending.

Figure 9:
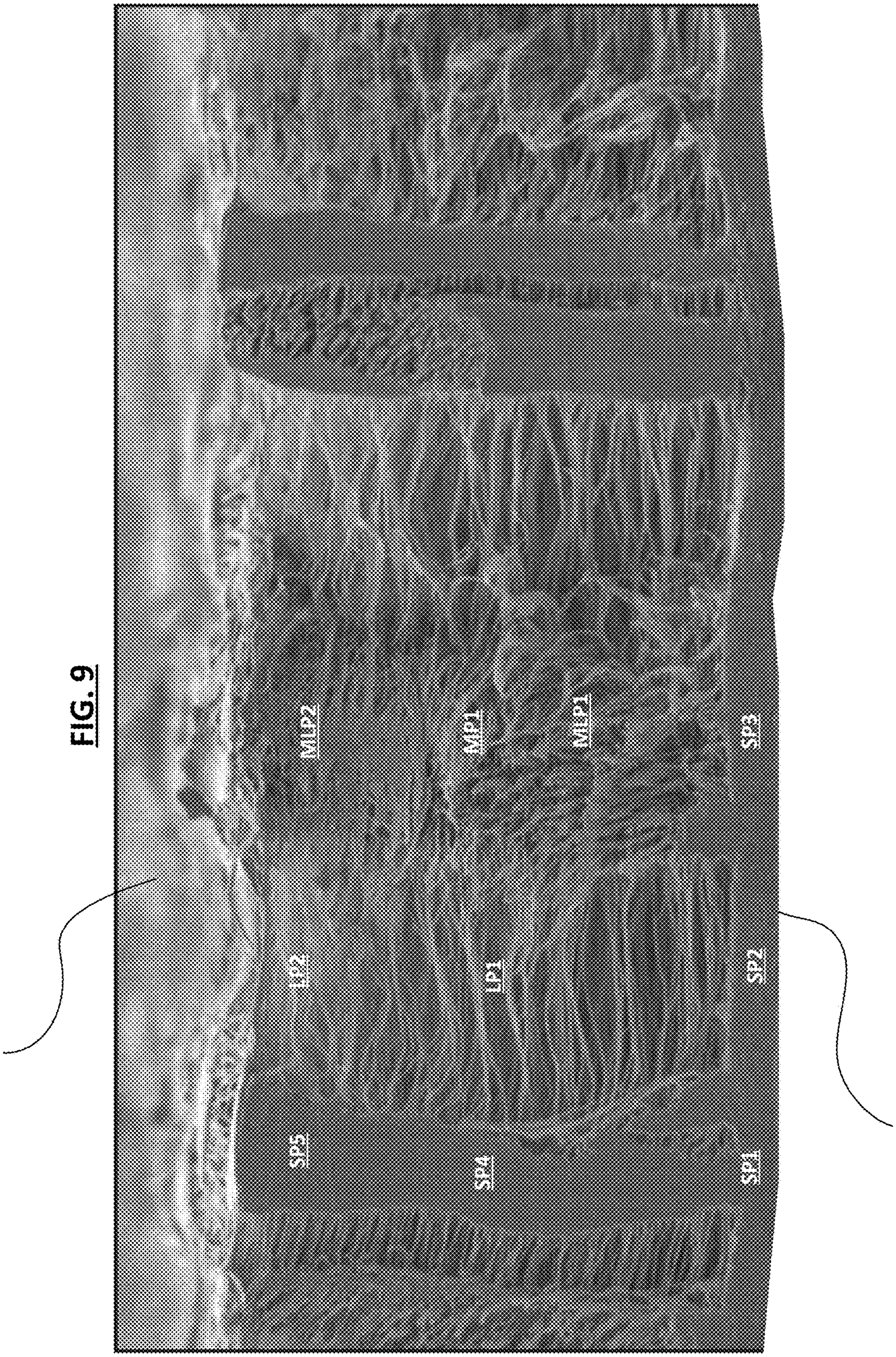
FIG. 9 is a close-up view of a microstructure in the drainage device of FIG. 3C according to some embodiments disclosed herein.

The body portion 202, or the layers 218 and 220 forming the body portion 202, may be made using a microporous material. As can be appreciated by a person of skill in the art and with reference to FIG. 9, the microporous aspects and parameters of the microporous material can be defined in a variety of ways. In an application of a microporous material in an ocular drainage device configured for in situ placement in the tissue of the eye to facilitate the draining of a biological fluid of the eye to maintain a healthy eye pressure, the microporous properties of such a microporous material can be generally characterized by a volumetric porosity value that can be defined as a ratio of a volume of the air or fluid defined by and contained within the microporous material as compared to an overall volume (or total volume) of the microporous material.

In another definition, a volumetric porosity can be defined as a percentage of the microporous material volume that is occupied by non-structural or transient elements such as air or other fluids. For example, a microporous material with an overall volume of 100 $mm^3$ and with 30 $mm^3$ of that volume comprising chambers holding air or a fluid would have a volumetric porosity value of 0.3 because 30% of the volume of the microporous material is empty or transient space that is filled with air or other fluids.

As can be appreciated, two microporous materials can have the same volumetric porosity but differ in the pore sizes presented to the incoming or exiting air or fluid. For example, a first material can a have a small number of large pores distributed over a fixed overall volume and a second material can have a relatively large number of relatively smaller pores distributed over the same fixed volume, and both microporous materials could have the same volumetric porosity if the air/fluid volume of the two materials are the same.

As can be further appreciated, the properties of the microporous materials used in an ocular drainage device can also be defined by the size of the passages passing through the microporous material or similarly defined as a pore size measured where a passage terminates at a surface of the microporous material or measured along a length of a passage within the material. Microporous materials with small pores or passages can impede flow through the material and comparatively large pores or passages can provide an increased pass through of the air or fluid into, out of, or within the microporous material.

As can be still further appreciated, the properties of the microporous material can also be defined by a tortuosity of the passages entering into and passing through the material, with relatively small or large passages presenting impeded fluid pathways due the frequency of turns in the passages or by the placement of obstructions in the fluid pathways. The air/fluid passthrough rates of a microporous material can be managed by controlling or defining any of the above-described characteristics of the material to provide a suitable material for use in an eye drainage application.

For simplicity, the aforementioned characteristics and variables of the microporous material used in the various embodiments and examples described herein can be presented simply as a porosity which can be based on a volumetric porosity, a pore or passage size, or a tortuosity metric. Again referring to FIG. 9, internal portions of the microporous material can have varying porosities (or volumetric porosities, or pore sizes, or tortuosities) as shown in FIG. 9, which is an expanded view of the circled section of the body portion 202 as shown in FIG. 3C. The internal portions can extend between the inner surface 308 and the outer surface 310.

At any of these portions of the body portion 202, the porosity can comparatively range in degree from small pore size (SP), medium-small pore size (MSP), medium pore size (MP), medium-large pore size (MLP), and large pore size (LP). Assuming, for discussion purposes here, that drainage travels along a relatively straight path through a microporous material so as to sequentially engage porosities of the inner surface 308, a uniform internal portion, and the outer surface 310, the combined flow resistance can be represented by likewise concatenating their respective porosities. For instance, the inner surface 308 typically has a low porosity throughout (e.g., to reduce, resist, or inhibit tissue ingrowth into the reservoir 204), and portions of the interior portions and the outer surface 310 can have any of the aforementioned degrees of porosity. Under these circumstances when the internal portion has a medium porosity and, for example, the internal portions have a medium porosity and the outer surface 310 has a high porosity, the flow passage through the microporous material from the reservoir 204 to tissue surrounding the device can be represented as SP-MP-LP. More examples are discussed here below.

Various flow paths can be present within the microporous material. Relatively linear flow paths may comprise regions SP1-SP4-SP5, for example or SP3-MLP1-MP1-MSP1. Under some conditions, e.g., where there is high pressure in the reservoir 204, at least some flow may proceed through the most direct path through the microporous material, such as SP1-SP4-SP5 or SP2-LP1-LP2. Although some flow paths may be relatively straight, there are also flow paths that are nonlinear. For instance, under certain conditions, at least some flow may proceed to flow through areas of increasingly less resistance such as SP1-LP1-LP2 or SP3-MLP1-LP1-LP2. As will be appreciated, the microstructure of the microporous materials may undergo modification processes to obtain certain types of flow through the microstructure. For instance, the microstructure may have relatively uniform layers across layered within the microstructure, or as shown here, have variable portions throughout the thickness of the microporous material.

In some examples, the body portion 202 defines a wall portion thickness extending between the inner surface 308 and the outer surface 310. The wall portion thickness can define an internal region of the body portion 202 having a transition porosity that is between a porosity of the low porosity surface (e.g., having smaller pore sizes) of the inner surface 308 and a porosity of the high porosity surface (e.g., having larger pore sizes) of the outer surface 310. In addition, or in alternative, the internal region can have an internal region porosity that is equal to porosities of the low porosity surfaces of the inner surface 308 and the outer surface 310. In addition, or in alternative, the internal region can have an internal region porosity that is equal to a porosity of the low porosity surface of the inner surface 308. In addition, or in alternative, the internal region can have an internal region porosity that is equal to a porosity of the high porosity surface of the outer surface 310.

Figure 10:
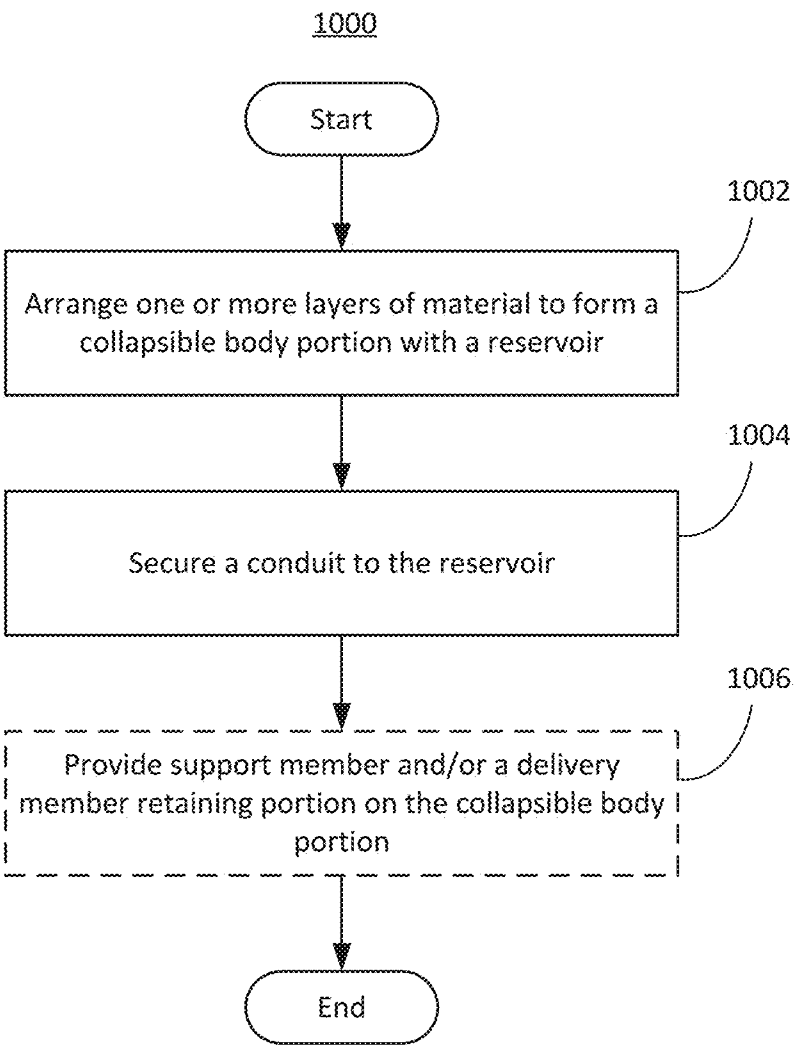
FIG. 10 is a flowchart of a method of manufacture consistent with various aspects of the present disclosure.

FIG. 10 shows a flowchart of a method 1000 consistent with aspects of the present disclosure. As shown, the method 1000 includes steps to form a drainage device implantable at least in part within a tissue of an eye. In step 1002, one or more layers of material is arranged to form a collapsible (for example, foldable, deformable, bendable, or crumplable) body portion with a reservoir defined therein. The reservoir is capable of receiving and accumulating biological fluid such as excess aqueous humor which may lead to unhealthy pressure buildups. In step 1004, a conduit is secured to the reservoir such that the first end of the conduit is fluidly coupled with the reservoir and the second end of the conduit can be inserted into the eye of the patient to facilitate drainage of the biological fluid into the conduit.

In some examples, the method 1000 may include additional step 1006 in which a support member and/or a retaining portion for a delivery member is provided. The support member and/or the retaining portion may be provided on the collapsible body portion. Numerous different types of support member and retaining portions may be implemented, as disclosed herein. For example, at least one support member may be provided where the support member includes an adsorbable material capable of adsorbing into the tissue of the eye in which the drainage device is implanted. In such cases, the at least one support member may be attached to an outer surface of the body portion.

In some examples, step 1006 involves inserting a portion of a delivery member into the reservoir via the conduit in order to facilitate the delivery of the drainage device to be implanted within the tissue of the eye. In some examples, the delivery member is retractable from the reservoir after the drainage device is implanted. The delivery member may be a flexible delivery wire including but not limited to a nickel-titanium alloy, or any suitable polymer including but not limited to nylon, for example.

In some examples, step 1006 involves forming the retaining portion for a delivery member on the body portion, and the retaining portion may be positioned outer or exterior to the reservoir and is disconnected from the reservoir. The retaining portion for the delivery member is capable of at least partially receiving a delivery member, for example at least a distal portion of the delivery member, in order to facilitate delivery of the drainage device to the tissue of the eye.

In some examples, the retaining portion for the delivery member can be a pocket formed partially in the body portion. The delivery member in such cases may have a curved portion at a distal end which is at least partially receivable by the pocket during the delivery.

In some examples, the retaining portion for the delivery member is a conduit formed to receive the delivery member, a.k.a. a delivery member conduit, on an outer surface of the body portion. The delivery member in such cases may be at least one flexible wire that is at least partially receivable within the delivery member conduit during the delivery. Step 1006 may further include positioning the delivery member conduit along a periphery of the reservoir or a periphery of the body member and/or positioning the delivery member conduit between the periphery of the reservoir and the periphery of the body member.

In some examples, the delivery member conduit may have a first opening capable of receiving a first flexible wire and a second opening capable of receiving a second flexible wire, and step 1006 may further include inserting the first flexible wire into the delivery member conduit via the first opening and also inserting the second flexible wire into the delivery member conduit via the second opening such that the first flexible wire and the second flexible wire overlap within the delivery member conduit during delivery of the drainage device.

Figure 11A:
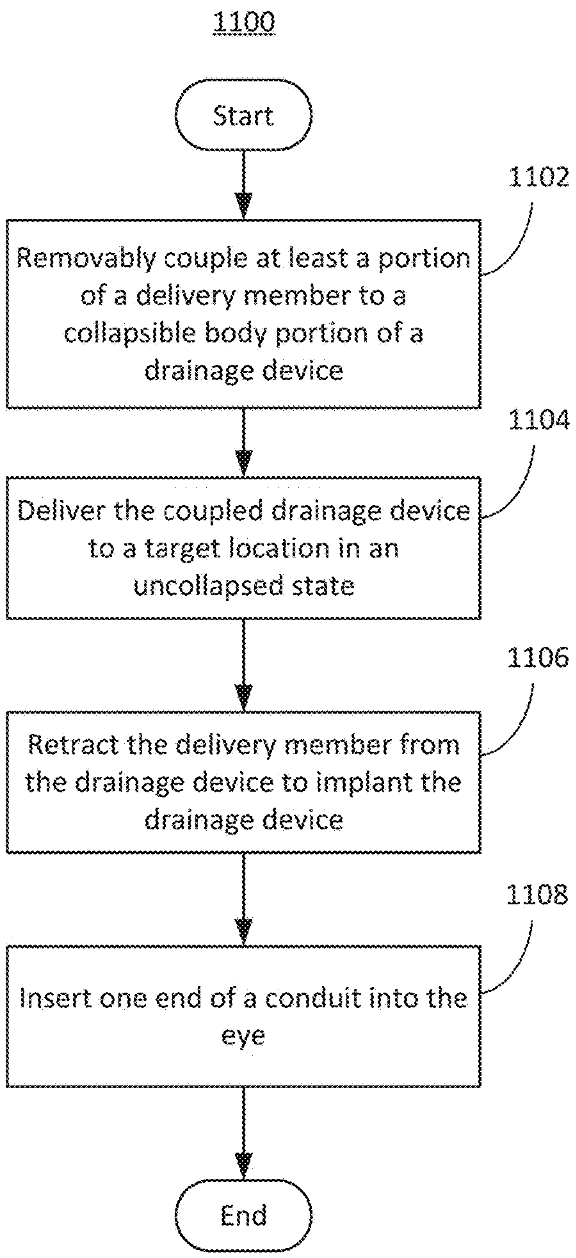
FIGS. 11A and 11B are flowcharts of methods of use consistent with various aspects of the present disclosure.

FIG. 11A shows a flowchart of a method 1100 consistent with aspects of the present disclosure. As shown, the method 1100 includes steps to treat glaucoma using a drainage device. In step 1102, at least a portion of a delivery member is removably coupled to a collapsible (for example foldable, deformable, bendable, or crumplable) body portion of the drainage device, and the body portion defines a reservoir capable of receiving and accumulating biological fluid therein. In step 1104, the delivery member is used to deliver the drainage device to a tissue of an eye to dispose the collapsible body portion in an uncollapsed state with a planar configuration. In some examples, the planar configuration is defined by a curved plane corresponding to a curvature of the eye. In step 1106, the delivery member is retracted from the drainage device in order to deploy the drainage device to be implanted at least in part (or entirely) within the tissue of the eye. In step 1108, the second end of a conduit is inserted into the eye to facilitate a drainage of the biological fluid (such as the aqueous humor within the eye) into the conduit. The first end of the conduit is secured to and fluidly coupled with the reservoir.

In some examples, the method 1100 may further include one or more additional step including attaching the drainage device to the tissue of the eye using at least one suture affixed to at least one suture hole on the body portion of the drainage device.

In some examples, step 1102 includes inserting a portion of the delivery member into the reservoir via the conduit in order to facilitate delivery of the drainage device to be implanted within the tissue of the eye. The delivery member may be retracted from the reservoir after the drainage device is implanted. In such cases, the delivery member may be any suitable flexible delivery wire including but not limited to that which is formed using a nickel-titanium alloy.

In some examples, step 1102 includes at least partially inserting the delivery member into a delivery member retaining portion formed on the body portion. The delivery member retaining position is positioned outside of the reservoir and disconnected from the reservoir. The delivery member retaining portion may be a pocket formed at least partially in the body portion, and the delivery member has a curved portion at a distal end which is at least partially receivable by the pocket during delivery.

In some examples, the retaining portion for the delivery member may be a delivery member conduit formed on an outer surface of the body portion. The delivery member may be at least one flexible wire at least partially receivable within the delivery member conduit. The delivery member conduit may be positioned along a periphery of the reservoir, along a periphery of the body member, and/or between the periphery of the reservoir and the periphery of the body member.

In some examples, the at least partially inserting the delivery member into the retaining portion for the delivery member, as per step 1102, may include inserting a first flexible wire into the delivery member conduit via a first opening of the delivery member conduit and inserting a second flexible wire into the delivery member conduit via a second opening of the delivery member conduit such that the first flexible wire and the second flexible wire overlap within the delivery member conduit during delivery of the drainage device.

Figure 11B:
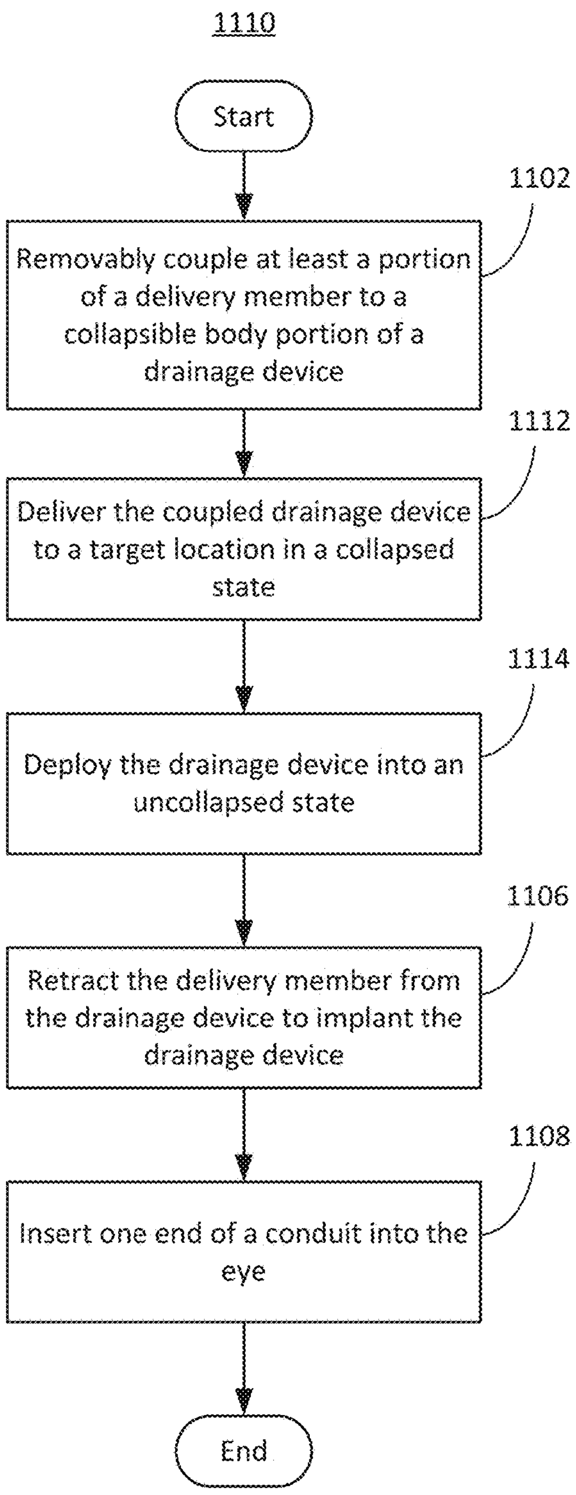

FIG. 11B shows a flowchart of another method 1110 consistent with aspects of the present disclosure. After step 1102 as previously explained, the coupled drainage device is delivered to a target location in its collapsed state, in step 1112. In step 1114, the drainage device is deployed into its uncollapsed state. The deploying may be performed by at least partially inflating the collapsed drainage device such that the drainage device assumes its uncollapsed state, for example. Alternatively, any other suitable method of uncollapsing the collapsed drainage device may be implemented. After the drainage device is uncollapsed, in step 1106, the delivery member is retracted from the drainage device to implant the drainage device and, in step 1108, one end of the conduit is inserted into the eye as previously explained.

Figure 12A:
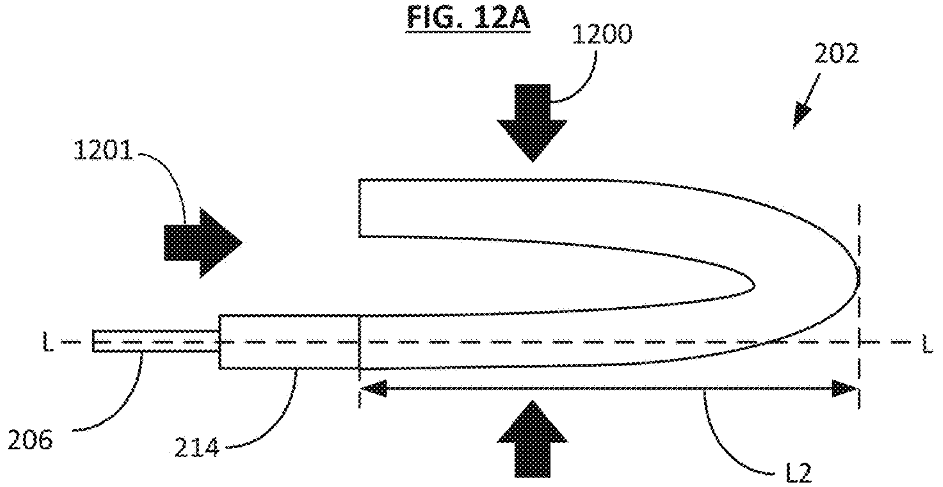
FIGS. 12A through 12C are side views of the drainage device when an external force is applied to fold the drainage device and after the external force is removed, according to some embodiments disclosed herein.
Figure 12B:
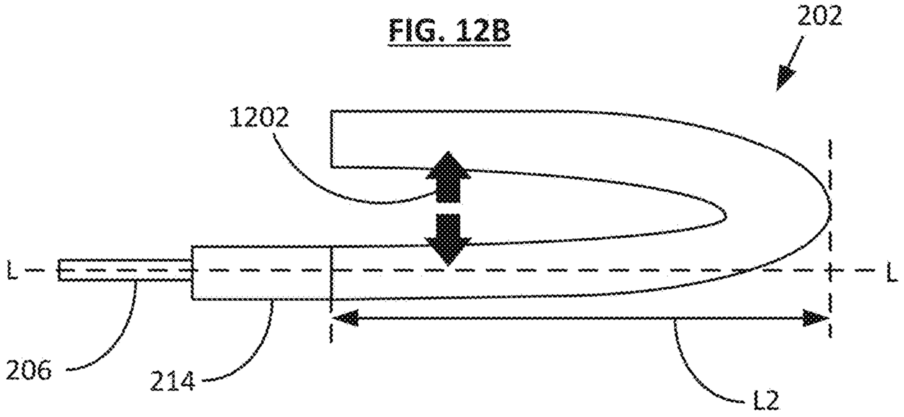
Figure 12C:
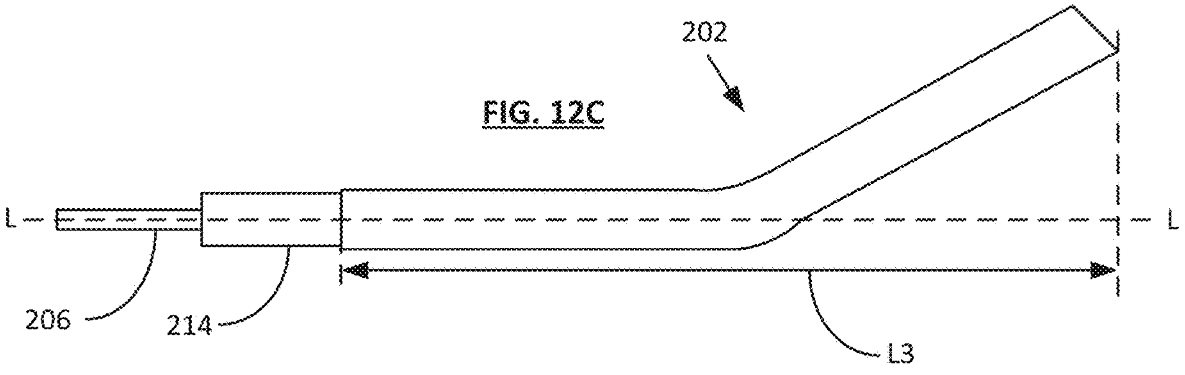

FIGS. 12A through 12C illustrate the stiffness/flexibility of an exemplary drainage device, or more specifically of the body portion thereof, in response to buckling, as well as the physical property to recover at least a portion of its full length after removal of an external force. In FIG. 12A, the body portion 202 is shown with an external collapsing force 1200 being applied to the body portion in the direction shown by the arrows directed toward the body portion. The external collapsing force 1200 may be a frictional force caused by pushing the body portion via a directional force 1201, for example a forward-moving force applied by a physician that is sufficient to push the body portion of the drainage device into a target tissue. As a result, the body portion is folded, bent, deformed, or buckled along the transverse axis T-T shown on FIG. 2B that is any axis which intersects the longitudinal axis L-L. The location of the folding (that is, the axis of the folding) is not necessarily positioned in or near the middle of the body portion; such folding may occur at any axis along the body portion including near the periphery 222 of the body portion. While the external force 1200 is applied, the body portion has a folded length “L2” that is shorter or less than the length “L1” which is the full length of the body portion.

FIG. 12B shows the body portion 202 immediately after the external collapsing force 1200 is removed. While the shape of the body portion remains the same, the body portion now exerts an internal or recovery force 1202 in a direction opposite of the external collapsing force 1200 (that is, away from the body portion in the example shown) which originates from the flexible physical property of the body portion. As such, the body portion, while in the folded configuration or folded state (also referred to as a nonplanar state), is capable of exerting a force to recover or return to its original configuration before the external collapsing force 1200 was applied.

FIG. 12C shows the body portion 202 at a certain time after the external collapsing force 1200 is removed, in the absence of any external force being exerted on the body portion. As shown, the recover force 1202 allowed the body portion to unfold at least partially such that the length of the body portion is now a longer length "L3" than the folded length L2. In some examples, the length L3 is referred to as the resting length of the body portion, defined as the length of the body portion after the external collapsing force 1200 was exerted to fold the body portion, then released such that the recovery force 1202 facilitates the folded body portion to unfold, until no further recovery force is observed.

As such, in some examples, L3 is the same as L1 (i.e., L3=L1), if the recovery force 1202 facilitates the full recovery of the body portion such that the final state of the body portion is substantially identical to the original state (for example, as shown in FIG. 2B).

Alternatively, in some examples, L3 is greater than L2 as the recovery force 1202 partially unfolds the body portion but not allowing the body portion to return to its original configuration when laid on a flat surface (i.e., L2<L3<L1). In such cases, L3 may be no greater than approximately 50%, 60%, 70%, 75%, 80%, 85%, 90%, or any other suitable range or value therebetween with respect to L1, such that a slight bend still remains in the body portion as shown in FIG. 12C.

In some cases, L3 may be defined by the length recovered from L2, which is the shortest length among L1, L2, and L3. That is, if the length of the body portion that is lost or shortened by folding is defined as (L1−L2), L3 may be mathematically defined as L3=L2+R(L1−L2), where R is the percentage (any value from 0% to 100%) of recovery achieved by the body portion as a result of the recovery force 1202. Therefore, if R=0, or if no recovery is observed, the result would be L3=L2. Alternatively, if R=1, or when there is a full recovery, the result would be L3=L1. In some examples, the value of R may be no greater than approximately 20%, 30%, 40%, 50%, 60%, 70%, 75%, 80%, 85%, 90%, or any other suitable value or range therebetween, when only partial recovery is observed. It is to be understood that L1, L2, and L3 are all measured along the same axis (e.g., the longitudinal axis L-L as shown) in order to provide accurate measurement of the folding/buckling as well as the recovery therefrom undergone by the body portion of the drainage device.

Figure 13:
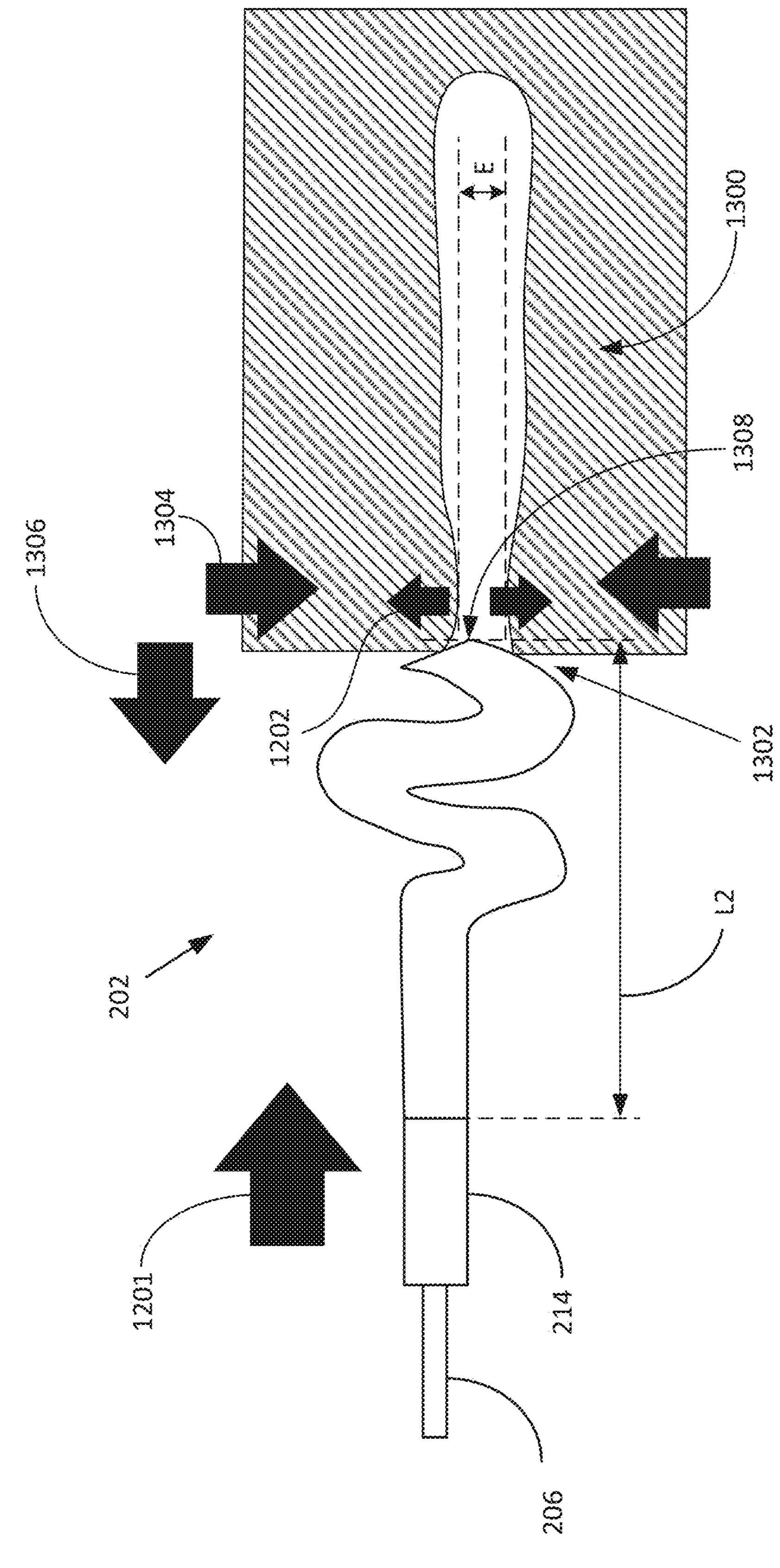
FIG. 13 is a side view of the drainage device that is partially collapsed when the drainage device is pushed forward to be inserted into the tissue of an eye, according to some embodiments disclosed herein.

FIG. 13 illustrates another example of how the body portion 202 of the drainage device may collapse in response to buckling, according to some embodiments. The directional force 1201, for example a forward-moving force applied by the physician, is applied to the body portion 202 in a direction effectively parallel to or along the longitudinal axis L-L toward a target tissue 1300. The target tissue may be the conjunctiva 13 of the patient's eye 10 (as shown in FIGS. 1C through 1H) into which the body portion may be inserted for treatment.

Figure 1C:
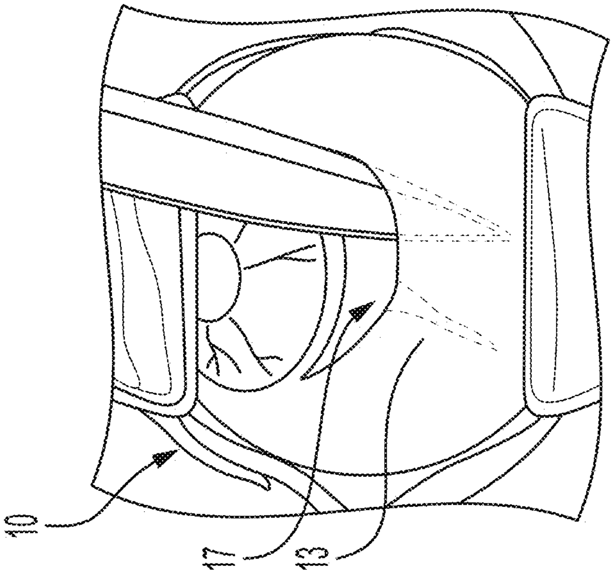
FIG. 1C (prior art)
FIGS. 1C through 1H are illustrations showing a process of implanting the prior-art glaucoma drainage device of FIG. 1A.
Figure 1D:
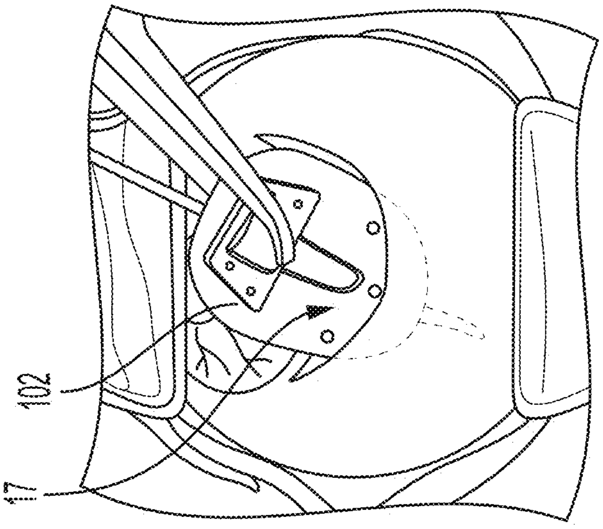
FIG. 1D (prior art)
Figure 1E:
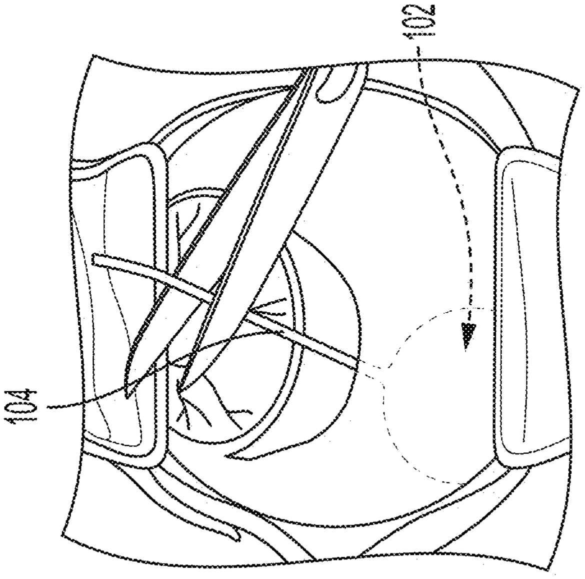
FIG. 1E (prior art)
Figure 1H:
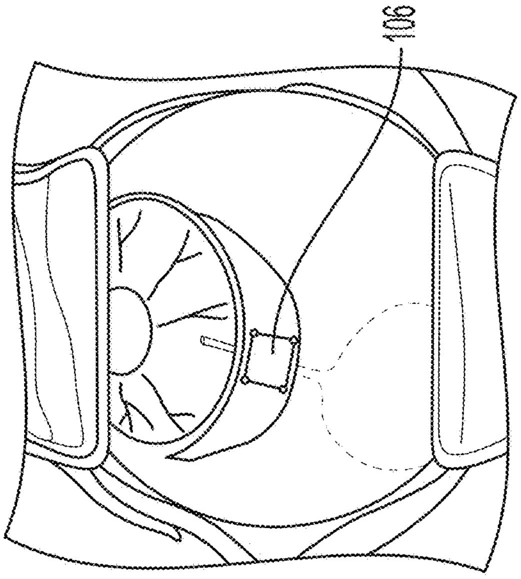
FIG. 1H (prior art)
Figure 1G:
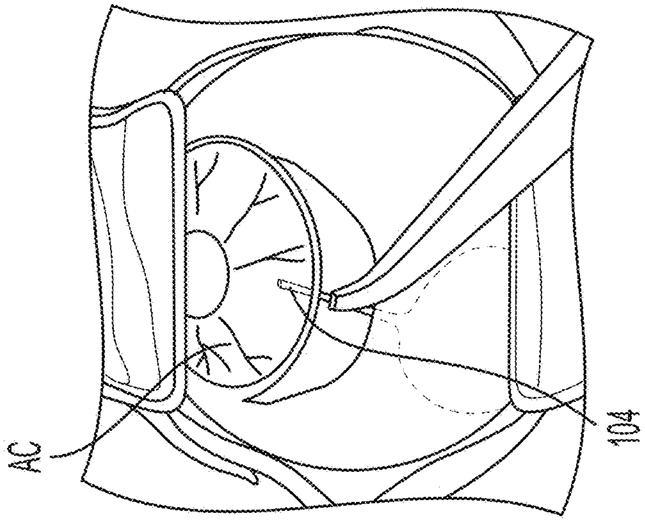
FIG. 1G (prior art)
Figure 1F:
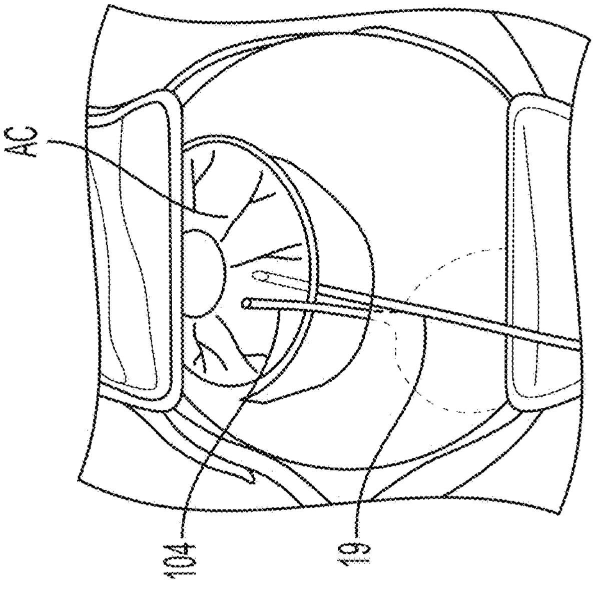
FIG. 1F (prior art)

The target tissue 1300 has an entrance 1302, which in some examples may be the opening formed by the fornix-based incision 17 that is made through the conjunctiva 13 of the patient's eye 10 using the scalpel as shown in FIG. 1C. The entrance may have a height "E" which is less than (i.e., narrower than) the maximum thickness "t2" of the body portion 202 of the drainage device such that, when the body portion attempts to enter through the entrance 1302, the entrance may impart a restrictive force 1304 which restricts the forward movement of the body portion therethrough. The restrictive force 1304 may be caused by the frictional force within the target tissue 1300 as well as by the size and shape of the entrance 1302 which would require a certain amount of force to overcome. That is, when a sufficient force is applied in the direction opposing the restrictive force 1304 so as to overcome the restrictive force, the entrance 1302 may open up further (either temporarily or permanently) to receive the body portion 202 of the drainage device. As such, the entrance 1302 is conformable depending upon the amount of force exerted against it, and the restrictive force 1304 is the minimal force required for a device to exert against the entrance 1302 in order for the device to be inserted through the entrance, if the device has a dimension that is large than the size of the entrance.

As the body portion 202 exerts the internal or recovery force 1202 in a direction opposite of the restrictive force 1304 exerted by the entrance 1302, it is observed that the recovery force 1202 of the body portion is less than the restrictive force 1304 of the entrance. Therefore, without having sufficient force to overcome the restrictive force, the body portion 202 is prevented from being inserted forward into the target tissue 1300. Instead, most, if not all, of the body portion 202 remains external to the target tissue, and as the directional force 1201 is continuously applied, the target tissue 1300 exerts a reactive force 1306 in a direction opposite to the directional force 1201. That is, the reactive force 1306 (which may be the frictional force exerted by the target tissue 1300 in response to the directional force 1201) prevents longitudinal distal movement of a distal end 1308 of the body portion 202, thereby causing the distal end of the body portion to remain outside the target tissue 1300 while the directional force 1201 is applied. The two opposing forces 1201 and 1306, therefore, cause the body portion 202 to collapse (or alternatively crumple, deform, bend, or fold as suitable) in the longitudinal direction (that is, a direction with respect to the longitudinal axis L-L) to shorten the longitudinal length of the body portion from L1 to L2 (where L2<L1) as the body portion 202 assumes a longitudinally collapsed configuration.

Any suitable biocompatible material may be used for the body portion and delivery member conduit, as discussed herein. In certain instances, the material may include a fluoropolymer, such as a polytetrafluoroethylene (PTFE) polymer or an expanded polytetrafluoroethylene (ePTFE) polymer. In some instances, the material may include, but is not limited to, a polyester, a silicone, a urethane, a polyethylene terephthalate, or another biocompatible polymer, or combinations thereof. In some instances, bioresorbable or bioabsorbable materials may be used, for example a bioresorbable or bioabsorbable polymer. In some instances, the material may include Dacron, polyolefins, carboxy methylcellulose fabrics, polyurethanes, or other woven, non-woven, or film elastomers.

In addition, nitinol (NiTi) may be used as the material of the delivery member(s) discussed herein, but other materials such as, but not limited to, stainless steel, L605 steel, polymers, MP35N steel, polymeric materials, Pyhnox, Elgiloy, or any other appropriate biocompatible material, and combinations thereof, may be used as the material of the frame. The super-elastic properties and softness of NiTi may enhance the conformability of the stent. In addition, NiTi may be shape-set into a desired shape. That is, NiTi may be shape-set so that the frame tends to self-expand into a desired shape when the frame is unconstrained, such as when the frame is deployed out from a delivery system.

The invention of this application has been described above both generically and with regard to specific embodiments. It will be apparent to those skilled in the art that various modifications and variations may be made in the embodiments without departing from the scope of the disclosure. Thus, it is intended that the embodiments cover the modifications and variations of this invention provided they come within the scope of the appended claims and their equivalents.

What is claimed is:

1. A drainage device for draining a biological fluid from an eye to a tissue external to the eye, the drainage device being implantable at least in part within a tissue of the eye and comprising:

a collapsible body portion defining a reservoir, wherein the collapsible body portion, when collapsed, includes a deformation of the body portion from a first planar state to a second nonplanar state; and a conduit having a first end fluidly coupled with the reservoir and a second end insertable into the eye to facilitate a drainage of the biological fluid into the conduit, wherein in situ the second nonplanar state is at least one of a folded state, a deformed state, a bent state, or a crumpled state, and wherein the collapsible body portion includes one or more of:

at least one temporary reinforcement element that maintains the collapsible body portion in the first planar state, wherein the at least one temporary reinforcement element is retractable from the collapsible body portion, or a retaining portion defined by the collapsible body portion, the retaining portion being sized and positioned to convey a pulling force to the collapsible body portion to maintain the collapsible body portion in the first planar state during implantation, wherein the retaining portion is configured to receive the pulling force from a delivery member.

2. A drainage device for draining a biological fluid from an eye to a tissue external to the eye, the drainage device being implantable at least in part within a tissue of the eye and comprising:

a collapsible body portion defining a reservoir, wherein the collapsible body portion, when collapsed, includes a deformation of the body portion from a first planar state to a second nonplanar state; and a conduit having a first end fluidly coupled with the reservoir and a second end insertable into the eye to facilitate a drainage of the biological fluid into the conduit, wherein in situ the second nonplanar state is at least one of a folded state, a deformed state, a bent state, or a crumpled state, and wherein during implantation the collapsible body portion includes at least one temporary reinforcement element that maintains the collapsible body portion in the first planar state, wherein the at least one temporary reinforcement element is retractable from the collapsible body portion.

3. The drainage device of claim 2, the collapsible body portion including a delivery member conduit formed on an outer surface of the collapsible body portion, wherein the temporary reinforcement element is at least one flexible wire partially received within the delivery member conduit.

4. The drainage device of claim 3, wherein the delivery member conduit is positioned along a periphery of the reservoir or a periphery of the body member.

5. The drainage device of claim 4, wherein the delivery member conduit is positioned between the periphery of the reservoir and the periphery of the body member.

6. The drainage device of claim 4, wherein the delivery member conduit comprises a first opening configured to receive a first temporary reinforcement element and a second opening is configured to receive a second temporary reinforcement element.

7. The drainage device of claim 6, wherein the first and second temporary reinforcement elements are configured to overlap within the delivery member conduit.

8. The drainage device of claim 3, wherein the delivery member is a flexible delivery wire including a nickel-titanium alloy.

9. The drainage device of claim 2, wherein the temporary reinforcement element is attached to an outer surface of the collapsible body portion, the temporary reinforcement element including an adsorbable material that is adsorbable into the tissue of the eye in which the drainage device is implanted.

10. The drainage device of claim 2, wherein the reservoir is able to receive a portion of the temporary reinforcement element via the conduit to facilitate delivery of the drainage device to be implanted within the tissue of the eye, the temporary reinforcement element being retractable from the reservoir after the drainage device is implanted.

11. The drainage device of claim 2, wherein the collapsible body portion is made of a microporous material.

12. The drainage device of claim 11, wherein the microporous material is expanded polytetrafluoroethylene (ePTFE).

13. The drainage device of claim 11, wherein the microporous material includes a plurality of subsections having various pore sizes.

14. The drainage device of claim 13, wherein the microporous material facilitates absorption of the biological fluid from the reservoir to be released to an outer environment surrounding the collapsible body portion.

15. The drainage device of claim 14, wherein the microporous material reduces tissue ingrowth from the outer environment into the reservoir.

16. The drainage device of claim 2, wherein the first planar state is defined by a curved plane corresponding to a curvature of the eye.

17. The drainage device of claim 2, wherein the collapsible body portion includes a material that is sufficiently flexible to deform in response to a directional force being applied to the body portion during implantation of the drainage device.

18. The drainage device of claim 17, wherein the collapsible body portion deforms in response to an external frictional force caused by the tissue of the eye when applying the directional force to the body portion during implantation of the drainage device.

19. The drainage device of claim 2, wherein the collapsible body portion has a first length in an uncollapsed state in absence of an external force, a second length less than the first length in a collapsed state when the external force is applied, and a third length greater than the second length and less than the first length in a resting state after the external force is removed.

20. The drainage device of claim 19, wherein the third length is no greater than approximately 90% of the first length.

21. The drainage device of claim 2, wherein the collapsible body portion is formed by at least partially adhering a periphery of a first body layer to a periphery of a second body layer.

22. The drainage device of claim 2, the collapsible body portion comprising at least one suture hole configured to receive a suture to facilitate attaching the drainage device to the tissue of the eye.

23. The drainage device of claim 2, the collapsible body portion further comprising at least one marker to mark a position of the conduit along the body portion.

24. The drainage device of claim 2, wherein the collapsible body portion has a thickness of no greater than about 0.5 mm around the reservoir when the reservoir is empty.

25. A drainage device for draining a biological fluid from an eye to a tissue external to the eye, the drainage device being implantable at least in part within a tissue of the eye and comprising:

a collapsible body portion defining a reservoir and a retaining portion, wherein the collapsible body portion, when collapsed, includes a deformation of the body portion from a first planar state to a second nonplanar state; and a conduit having a first end fluidly coupled with the reservoir and a second end insertable into the eye to facilitate a drainage of the biological fluid into the conduit, wherein in situ the second nonplanar state is at least one of a folded state, a deformed state, a bent state, or a crumpled state, and wherein the retaining portion of the collapsible body portion is sized and positioned to convey a pulling force to the collapsible body portion to maintain the collapsible body portion in the first planar state during implantation, wherein the retaining portion is configured to receive the pulling force from a delivery member.

26. The drainage device of claim 25, wherein the retaining portion is a pocket formed partially in the collapsible body portion, and the delivery member has a curved portion at a distal end which is partially received by the pocket.

27. The drainage device of claim 25, wherein the first planar state is defined by a curved plane corresponding to a curvature of the eye.

28. The drainage device of claim 25, wherein the collapsible body portion includes a material that is sufficiently flexible to deform in response to a directional force being applied to the body portion during implantation of the drainage device.

29. The drainage device of claim 27, wherein the collapsible body portion deforms in response to an external frictional force caused by the tissue of the eye when applying the directional force to the body portion during implantation of the drainage device.

30. The drainage device of claim 25, wherein the collapsible body portion has a first length in an uncollapsed state in absence of an external force, a second length less than the first length in a collapsed state when the external force is applied, and a third length greater than the second length and less than the first length in a resting state after the external force is removed.

31. The drainage device of claim 30, wherein the third length is no greater than approximately 90% of the first length.

32. The drainage device of claim 25, wherein the collapsible body portion is formed by at least partially adhering a periphery of a first body layer to a periphery of a second body layer.

33. The drainage device of claim 25, the collapsible body portion comprising at least one suture hole configured to receive a suture to facilitate attaching the drainage device to the tissue of the eye.

34. The drainage device of claim 25, the collapsible body portion further comprising at least one marker to mark a position of the conduit along the body portion.

35. The drainage device of claim 25, wherein the delivery member is a flexible delivery wire including a nickel-titanium alloy.

36. The drainage device of claim 25, wherein the collapsible body portion has a thickness of no greater than about 0.5 mm around the reservoir when the reservoir is empty.

* * * * *